(12) United States Patent
Barbieri et al.

(10) Patent No.: US 11,075,009 B2
(45) Date of Patent: Jul. 27, 2021

(54) SYSTEM AND METHOD FOR SYMPATHETIC AND PARASYMPATHETIC ACTIVITY MONITORING BY HEARTBEAT

(71) Applicant: The General Hospital Corporation, Boston, MA (US)

(72) Inventors: Riccardo Barbieri, Boston, MA (US); Luca Citi, London (GB); Gaetano Valenza, Pisa (IT)

(73) Assignee: The General Hospital Corporation, Boston, MA (US)

( * ) Notice: Subject to any disclaimer, the term of this patent is extended or adjusted under 35 U.S.C. 154(b) by 20 days.

(21) Appl. No.: 15/749,838

(22) PCT Filed: Jul. 29, 2016

(86) PCT No.: PCT/US2016/044844
§ 371 (c)(1),
(2) Date: Feb. 2, 2018

(87) PCT Pub. No.: WO2017/027232
PCT Pub. Date: Feb. 16, 2017

(65) Prior Publication Data
US 2018/0233234 A1    Aug. 16, 2018

Related U.S. Application Data

(60) Provisional application No. 62/204,406, filed on Aug. 12, 2015, provisional application No. 62/260,834, filed on Nov. 30, 2015.

(51) Int. Cl.
*A61B 5/00* (2006.01)
*G16H 50/50* (2018.01)
(Continued)

(52) U.S. Cl.
CPC ......... *G16H 50/50* (2018.01); *A61B 5/02405* (2013.01); *A61B 5/04012* (2013.01);
(Continued)

(58) Field of Classification Search
CPC .......... G16H 50/50; A61B 5/746; A61B 5/40; A61B 5/4035–4076; A61B 5/7264;
(Continued)

(56) References Cited

U.S. PATENT DOCUMENTS 5,313,953 A    5/1994  Yomtov
7,079,888 B2   7/2006  Oung
(Continued)

OTHER PUBLICATIONS

Vetter R, et al. Observer of autonomic cardiac outflow based on blind source separation of ecg parameters. Biomedical Engineering IEEE Transactions on 2000;47(5):578-582.
(Continued)

*Primary Examiner* — Scott M. Getzow
(74) *Attorney, Agent, or Firm* — Quarles & Brady LLP

(57) ABSTRACT

A system and method for analyzing a subject health condition based on an input signal comprising subject heartbeat data recorded from the subject over a time period. Using the subject heartbeat data, a sympathetic activity index value in a sympathetic activity index (SAI) determined, where the SAI represents an influence, on a mean heart rate of the subject, of sympathetic nerve activity (SNA) of the subject.

17 Claims, 7 Drawing Sheets

(51) Int. Cl.
   *A61B 5/024*   (2006.01)
   *A61B 5/04*   (2006.01)
   *A61B 5/0456*   (2006.01)
   *A61B 5/0245*   (2006.01)
   *A61B 5/16*   (2006.01)

(52) U.S. Cl.
   CPC .......... *A61B 5/0456* (2013.01); *A61B 5/7264* (2013.01); *A61B 5/7282* (2013.01); *A61B 5/746* (2013.01); *A61B 5/0245* (2013.01); *A61B 5/165* (2013.01); *A61B 5/4806* (2013.01)

(58) Field of Classification Search
   CPC . A61B 5/0456; A61B 5/04012; A61B 5/4806; A61B 5/165; A61B 5/02405; A61B 5/7282; A61B 5/0245
   See application file for complete search history.

(56) References Cited

U.S. PATENT DOCUMENTS

| | | | |
|---|---|---|---|
| 8,577,456 | B2 | 11/2013 | Maskara |
| 2006/0100534 | A1 | 5/2006 | Colombo |
| 2007/0219455 | A1* | 9/2007 | Wong .................. A61B 5/02405 600/515 |
| 2008/0287812 | A1 | 11/2008 | Parlikar |
| 2009/0069647 | A1 | 3/2009 | McNames |
| 2009/0318983 | A1 | 12/2009 | Armoundas |
| 2012/0123232 | A1 | 5/2012 | Najarian |
| 2014/0031651 | A1 | 1/2014 | Chon |
| 2014/0058471 | A1 | 2/2014 | Maskara et al. |
| 2014/0207005 | A1 | 7/2014 | Bukkapatnam et al. |
| 2015/0080670 | A1* | 3/2015 | Osorio .................. A61B 5/7275 600/301 |

OTHER PUBLICATIONS

Vetter R, et al. Observer of the human cardiac sympathetic nerve activity using noncausal blind source separation. Biomedical Engineering IEEE Transactions on 1999;46(3):322-330.

Yasuma F. et al, "Respiratory sinus arrhythmia*," Chest, vol. 125, No. 2, pp. 683-690,2004.

Zhong, Y., et al. "Nonlinear analysis of the separate contributions of autonomic nervous systems to heart rate variability using principal dynamic modes." IEEE transactions on biomedical engineering 51.2 (2004): 255-262.

Zhong, Y., et al. "Quantifying cardiac sympathetic and parasympathetic nervous activities using principal dynamic modes analysis of heart rate variability." American Journal of Physiology-Heart and Circulatory Physiology 291.3 (2006): H1475-H1483.

Zong W. et al, "Wqrs-single-channel qrs detector based on length transform," Physionet. http://www.physionet.org/physiotools/wag/wqrs-1.htm, 2003. Version last updated May 28, 2015.

Akselrod S., "Components of heart rate variability: basic studies," Heart Rate Variability, Chapter 12. pp. 147-163, 1995.

Akselrod, S. et al, "Hemodynamic regulation: investigation by spectral analysis," American Journal of Physiology-Heart and Circulatory Physiology, vol. 249, No. 4, p. H867, 1985.

Akselrod, S. et al, "Power spectrum analysis of heart rate fluctuation: a quantitative probe of beat-to-beat aardiovascular control," Science, vol. 213, No. 4504, p. 220, 1981.

Altini, M. Heart Rate Variability for Training. 2013. Accessed on Apr. 4, 2015 at http://www.marcoaltini.com/blog/heart-rate-variability.

Atyabi, F., et al. "Two statistical methods for resolving healthy individuals and those with congestive heart failure based on extended self-similarity and a recursive method." Journal of biological physics 32.6 (2006): 489-495.

Barbieri R. et al, "Analysis of heartbeat dynamics by point process adaptive filtering," Biomedical Engineering, IEEE Transactions on, vol. 53, No. 1, pp. 4-12, 2006.

Barbieri, R. et al, "A point-process model of human heartbeat intervals: new definitions of heart rate and heart rate variability," American Journal of Physiology-Heart and Circulatory Physiology, vol. 288, No. 1, p. H424, 2005.

Berger, R. et al, "Transfer function analysis of autonomic regulation. i. canine atrial rate response," American Journal of Physiology-Heart and Circulatory Physiology, vol. 256, No. 1, p. H142, 1989.

Brown, E. et al, "The time-rescaling theorem and its application to neural spike train data analysis," Neural Computation, vol. 14, No. 2, pp. 325-346, 2002.

Cavalcanti S. et al, "Modeling of cardiovascular variability using a differential delay equation," Biomedical Engineering, IEEE Transactions on, vol. 43, No. 10, pp. 982-989, 1996.

Chen X. et al, "Selective quantification of the cardiac sympathetic and parasympathetic nervous systems by multisignal analysis of cardiorespiratory variability," American Journal of Physiology-Heart and Circulatory Physiology, vol. 294, No. 1, p. H362, 2008.

Chess, G. et al, "Influence of cardiac neural inputs on rhythmic variations of heart period in the cat," American Journal of Physiology—Legacy Content, vol. 228, No. 3, p. 775, 1975.

Choi, J., et al. "Estimating mental stress using a wearable cardiorespiratory sensor." Sensors, 2010 IEEE. IEEE, 2010.

Choi, J., et al. "Estimating the principal dynamic modes of autonomic state with wearable sensors." Technical Report tamu-cs-tr-2008-7-2 (2008).

Choi, J., et al. "Removal of respiratory influences from heart rate variability in stress monitoring." IEEE Sensors Journal 11.11 (2011): 2649-2656.

Choi, J., et al. "Using heart rate monitors to detect mental stress." 2009 Sixth International Workshop on Wearable and Implantable Body Sensor Networks. IEEE, 2009.

Choi, J., et al. "Development and evaluation of an ambulatory stress monitor based on wearable sensors." IEEE transactions on information technology in biomedicine 16.2 (2011): 279-286.

Citi, L. et al. "A real-time automated point-process method for the detection and correction of erroneous and ectopic heartbeats." IEEE transactions on biomedical engineering 59.10 (2012): 2828-2837.

Cornforth, D. et al. "Automated selection of measures of heart rate variability for detection of early cardiac autonomic neuropathy." Computing in Cardiology 2014. IEEE, 2014.

Deboer, R. et al, "Beat-to-beat variability of heart interval and blood pressure," Automedica Lond, vol. 4, pp. 217-222, 1983.

Deboer, R. et al, "Hemodynamic fluctuations and baroreflex sensitivity in humans: a beat-to-beat model," American Journal of Physiology-Heart and Circulatory Physiology, vol. 253, No. 3, p. H680, 1987.

DSI Heart Rate Variability. Webpage. Accessed Feb. 9, 2015 online at https://www.datasci.com/solutions/cardiovascular/heart-rate-variability-(hrv).

Gutiérrez-Tobal, GC, et al. "Assessment of time and frequency domain entropies to detect sleep apnoea in heart rate variability recordings from men and women." Entropy 17.1 (2015): 123-141.

Guyton A. et al, "Pressoreceptor-autonomic oscillation: a probable cause of vasomotor waves," American Journal of Physiology—Legacy Content, vol. 165, No. 1, p. 158, 1951.

Hainsworth R., "The control and physiological importance of heart rate," Heart rate variability Chapter 1, pp. 3-19, 1995.

Hirsch J. et al, "Respiratory sinus arrhythmia in humans: how breathing pattern modulates heart rate," American Journal of Physiology-Heart and Circulatory Physiology, vol. 241, No. 4, p. H620, 1981.

Houle M. et al, "Low-frequency component of the heart rate variability spectrum: a poor marker of sympathetic activity," American Journal of Physiology-Heart and Circulatory Physiology, vol. 276, No. 1, p. H215, 1999.

International Searching Authority, International Search Report and Written Opinion for application PCT/US2016/044844. dated Oct. 21, 2016.

Kamath M. et al, "Power spectral analysis of heart rate variability: a noninvasive signature of cardiac autonomic function." Critical reviews in biomedical engineering, vol. 21, No. 3, p. 245, 1993.

Koepchen H. et al, "History of studies and concepts of blood pressure waves," Mechanisms of blood pressure waves, pp. 3-23, 1984.

(56) References Cited

OTHER PUBLICATIONS

Levy M. et al, "Autonomic control of cardiac pacemaker activity and atrioventricular transmission," Journal of Applied Jhysiology, vol. 27, No. 4, p. 465, 1969.
Levy M., "Sympathetic—parasympathetic interactions in heart," Circ. Res., vol. 29, No. 437, 1971.
Malliani A., "Association of heart rate variability components with physiological regulatory mechanisms," Heart rate variability, pp. 173-188, 1995.
Malliani, A. et al, "Cardiovascular neural regulation explored in the frequency domain," Circulation, vol. 84, No. 2, p. 482, 1991.
Malliani, A. et al, "Cardiovascular variability is/is not an index of autonomic control of circulation," Journal of Applied Physiology, vol. 101, pp. 684-688, 2006.
Malpas S., "Neural influences on cardiovascular variability: possibilities and pitfalls," American Journal of Physiology-Heart and Circulatory Physiology, vol. 282, No. 1, p. H6, 2002.
Mansier, P. et al, "Linear and non-linear analyses of heart rate variability: a minireview," Cardiovascular research, vol. 31, No. 3, p. 371, 1996.
Marmarelis V. et al, "Identification of nonlinear biological system using laguerre expansions of kernels," Ann. Biomed. Eng., vol. 21, pp. 573-589, 1993.
Mullen, T. et al, "System identification of closed-loop cardiovascular control: effects of posture and autonomic blockade," American Journal of Physiology-Heart and Circulatory Physiology, vol. 272, No. 1, pp. H448-H461, 1997.
Peng, R-C, et al. "Extraction of heart rate variability from smartphone photoplethysmograms." Computational and mathematical methods in medicine 2015 (2015).
Pomeranz, B. et al., "Assessment of autonomic function in humans by heart rate spectral analysis," American Journal of Physiology-Heart and Circulatory Physiology, vol. 248, No. 1, p. H151, 1985.
Rawenwaaij-Arts, C., et al. "Heart rate variability." Annals of internal medicine 118.6 (1993): 436-447.
Ruediger, H., et al. "Sympathetic and parasympathetic activation in heart rate variability in male hypertensive patients under mental stress." Journal of human hypertension 18.5 (2004): 307-315.
Saul, J. et al, "Transfer function analysis of the circulation: unique insights into cardiovascular regulation," American Journal of Physiology-Heart and Circulatory Physiology, vol. 261, No. 4, p. H1231, 1991.
Sayers B., "Analysis of heart rate variability." Ergonomics, vol. 16, No. 1, p. 17, 1973.
Schwartz P. et al, "Sympathetic—parasympathetic interaction in health and disease: abnormalities and relevance in heart failure," Heart failure reviews, pp. 1-7, 2010.
Seydnejad S. et al, "Modeling of mayer waves generation mechanisms," Engineering in Medicine and Biology Magazine, IEEE, vol. 20, No. 2, pp. 92-100, 2001.
Taylor, J. et al, "Mechanisms underlying very-low-frequency rr-interval oscillations in humans," Circulation, vol. 98, No. 6, pp. 547-555, 1998.
Ursino M. et al, "Role of short-term cardiovascular regulation in heart period variability: a modeling study," American Journal of Physiology-Heart and Circulatory Physiology, vol. 284, No. 4, p. H1479, 2003.
Valenza, G., et al. "Point-process nonlinear models with laguerre and volterra expansions: Instantaneous assessment of heartbeat dynamics." IEEE Transactions on Signal Processing 61.11 (2013): 2914-2926.

\* cited by examiner

SYSTEM AND METHOD FOR SYMPATHETIC AND PARASYMPATHETIC ACTIVITY MONITORING BY HEARTBEAT

CROSS-REFERENCE TO RELATED APPLICATIONS

This application represents the national stage entry of PCT International Application PCT/US2016/044844 filed Jul. 29, 2016, which claims benefit of U.S. Provisional Application 62/204,406 filed Aug. 12, 2015 and U.S. Provisional Application 62/260,834 filed Nov. 30, 2015, all of which is incorporated herein in its entirety by reference.

BACKGROUND

Algorithms for processing heartbeat variations, such as heart rate variability (HRV), have been of growing importance for developing real-time applications able to use simple, noninvasive sensors to monitor cardiovascular health, emotional or physiological states, quality of sleep, exercise performance, and the like. Such applications can collect data in clinical settings, as well as in non-clinical settings when the heartbeat can be acquired using single-channel miniature devices, smartphones, or wearable technology. In this regard, only rudimentary concepts and very simple computational algorithms associated with HRV have been used for clinical monitoring, and the few mobile applications for non-clinical settings provide only very imprecise, unreliable assessments of stress levels, sleep quality, or recovery from athletic activity. In both cases, the main reason for such failure can be attributed to the fact that current autonomic measures have very high inter-individual variability. Such measures do not provide meaningful markers that are valid for group analysis and are tailored to the individual at the same time.

Cardiovascular control is directed primarily at maintaining arterial blood pressure (ABP) in the face of changes in peripheral blood flow demand. A key role is taken by the autonomic nervous system (ANS), through the sympathetic and parasympathetic (vagus) branches. Since these nerves effect on the sinus node in the heart, autonomic outflow is reflected on intantaneous heartbeat variations. Heart rate (HR), commonly measured by detecting R-waves from the electrocardiogram (ECG), is modulated by centrally mediated autonomic reflexes to control ABP. HRV is the variation of HR about its mean, and is an important marker of cardiovascular regulation by the ANS. Due to inability of the cardiac response to sympathetic drive at high frequencies (HF) of 0.15-0.4 Hz, the HRV respiratory-associated oscillations (i.e., respiratory sinus arrhythmia (RSA)) are mediated via the vagus nerve, with further evidence of central coupling of respiratory drive to cardiac vagal motor neurons. Slower ABP and HR oscillations (low frequencies (LF) of 0.04-0.15 Hz) may reflect either a central oscillator model or, more commonly, closed-loop compensatory slow changes mediated by baroreceptors (Baroreflex) mediated by both autonomic branches. This "dual mediation" causes a significant overlap of sympathetic and parasympathetic activity in the LF band. Conventional spectral analysis of HRV is hindered by this overlap, and does not accurately reflect the separate influences of the sympathetic and parasympathetic branches of the ANS.

The study of HRV has brought significant clinical advances in the last decades, and measures of HRV are popularly used in current research to diagnose diseases that affect the ANS, follow their progression, and measure efficacy of therapy. HRV analysis has also yielded important insights into cardiovascular control assessment, characterizing cardiovascular responses and causal relations among cardiovascular and respiratory variables, with particular attention to time-varying assessment, as well as measures of RSA and Baroreflex. Furthermore, nonlinear and scale-invariant characterizations of HRV have pointed at important measures of cardiovascular control complexity and have been of useful prognostic value in aging and disease. Despite all these advances, HRV assessment has been lacking in providing precise measures of autonomic activity that can overcome the large inter-subject variability, with consequent inaccurate instantaneous individual assessments. In addition, despite a few encouraging attempts, no methodology so far has been able to provide a separate independent assessment of vagal and sympathetic instantaneous dynamics that can be (a) obtained exclusively from the heartbeat, (b) universally applied to a wide range of subjects, and (c) specifically tailored to the individual.

SUMMARY

The present disclosure provides devices and methods based on real-time assessment of independent vagal and sympathetic dynamics from the heartbeat interval. Given a heartbeat event, which can be detected from several sources (i.e. Electrocardiogram, Ecocardiogram, Photopletimographic Pulse Signal, Video Camera Signal, Ballistogram, Ultra Wideband Cardiogram etc.), the influence of the two autonomic branches on heartbeat dynamics is tracked within a sequential/feedback framework for constructing a tree-like decisional structure. The framework is not only able to provide a comprehensive autonomic instantaneous assessment based on separate instantaneous estimates of sympathetic activity and parasympathetic activity, but it also provides specific novel instantaneous features associated with a wide range of individual subject's conditions as dependent on his autonomic state. These features are appropriately combined within unique classification or stratification procedures to implement an evaluation module suitable to the subject's conditions and the environment, including, without limitation, modules for analysis during sleep, anesthesia, stress, emotional states, and exercise/sport, as well as monitoring for alarm conditions (e.g., in an intensive care unit (ICU) environment). The devices and associated executable program instructions may require a user to simply provide an input signal containing the subject's heartbeat, and the devices return the estimates of sympathetic and parasympathetic activity as output.

In accordance with one aspect of the disclosure, a computing device is provided that includes an input device interface configured to receive an input signal comprising subject heartbeat data recorded from a subject, a processor in signal communication with the input device interface, and memory storing program instructions. The processor executes the program instructions to determine a set of heartbeat events from the subject heartbeat data, the heartbeat events including a plurality of past R-R intervals and generate a first model of a mean heart rate of the subject. The first model includes a modeling function that includes a time-varying zero-order autoregressive coefficient and a sympathetic component representing an influence on the mean heart rate of the subject's sympathetic nerve activity. The sympathetic component includes a first sum, computed at a first frequency, of a time-varying first-order autoregressive coefficient multiplying a Laguerre expansion of the plurality of past R-R intervals. The modeling function further includes a parasympathetic component representing an influence on the mean heart rate of the subject's parasympathetic nerve activity. The parasympathetic component includes a second sum, computed at a second frequency, of the first-order autoregressive coefficient multiplying the Laguerre expansion. The first model further includes a modeling structure including a first function of the first-order autoregressive coefficient within the sympathetic component, and a second function of the first-order autoregressive coefficient within the parasympathetic component. The processor is further programmed to calculate a plurality of recursive parameter estimations of the first function to generate a first time-varying estimation of the modeling structure, calculate a plurality of recursive parameter estimations of the second function to generate a second time-varying estimation of the modeling structure, and determine a first multiple regression of the first function to generate a first disentangling coefficient. The processor is further programmed to determine a second multiple regression of the second function to generate a second disentangling coefficient, determine a sympathetic activity index value in a sympathetic activity index (SAI) defined by a SAI function that includes the first disentangling coefficient and the first time-varying estimation of the modeling structure, and determine a parasympathetic activity index value in a parasympathetic activity index (PAI) defined by a PAI function that includes the second disentangling coefficient and the second time-varying estimation of the modeling structure.

In accordance with one aspect of the disclosure, a computing device is provided that includes an interface configured to receive an input signal comprising subject heartbeat data recorded from a subject over a period of time, a processor in signal communication with the interface, and memory storing program instructions. The processor executes the program instructions to determine, from the subject heartbeat data, a sympathetic activity index value in a SAI. The SAI represents an influence, on a mean heart rate of the subject, of sympathetic nerve activity (SNA) of the subject, the SNA occurring during the time period.

In accordance with one aspect of the disclosure, a method is provided that obtains a set of heartbeat events including a plurality of past R-R intervals and generates a first model of a mean heart rate from the set of heartbeat events. The first model has a sympathetic component representing an influence of sympathetic nerve activity on the mean heart rate, where the sympathetic component has a time-varying first autoregressive coefficient and a Laguerre expansion of the plurality of past R-R intervals. The first model is also comprised of a parasympathetic component that represents an influence of sympathetic nerve activity on the mean heart rate. The parasympathetic component has a time-varying second autoregressive coefficient and the Laguerre expansion. The first model also has a modeling structure that includes a first function of the first autoregressive coefficient and a second function of the second autoregressive coefficient. Based on the first function, a sympathetic activity index value is determined in a sympathetic activity index (SAI). Based on the second function, a parasympathetic activity index value is determined in a parasympathetic activity index (PAI).

In accordance with another aspect of the disclosure, a system is provided for monitoring a condition of a patient. The system has an input configured to receive a signal indicative of a heartbeat of a subject, and a processor in communication with the input to receive the signal. The system is configured to analyze the signal to identify an autonomic state of the subject by evaluating sympathetic and parasympathetic activity of the subject. Additionally, the system uses a predetermined model and the autonomic state to generate an index of dynamics of two autonomic branches, and generate a report of a current condition of the subject based on the index.

DETAILED DESCRIPTION

Figure 1:
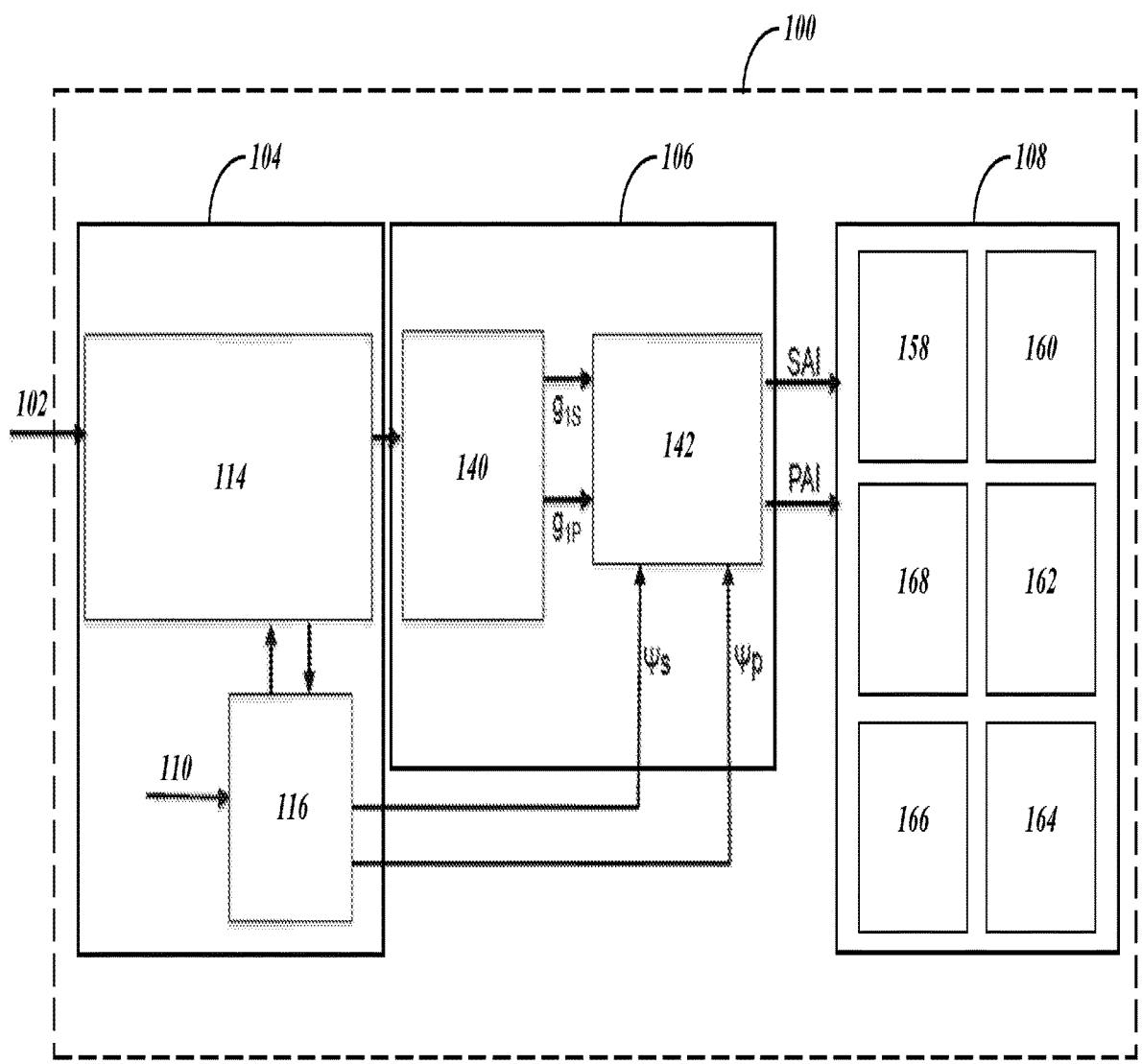
FIG. 1 is a diagram of a device implementing an embodiment of a sympathetic and parasympathetic activity monitoring system in accordance with the present disclosure.

The following discussion is presented to enable a person skilled in the art to make and use embodiments of the invention. Various modifications to the illustrated embodiments will be readily apparent to those skilled in the art, and the generic principles herein can be applied to other embodiments and applications without departing from embodiments of the invention. Thus, embodiments of the invention are not intended to be limited to embodiments shown, but are to be accorded the widest scope consistent with the principles and features disclosed herein. The following detailed description is to be read with reference to the figures. The figures depict selected embodiments and are not intended to limit the scope of embodiments of the invention. Skilled artisans will recognize the examples provided herein have many useful alternatives and fall within the scope of embodiments of the invention.

The following description refers to elements or features being "connected" or "coupled" together. As used herein, unless expressly stated otherwise, "connected" means that one element/feature is directly or indirectly connected to another element/feature, and not necessarily mechanically. Likewise, unless expressly stated otherwise, "coupled" means that one element/feature is directly or indirectly coupled to another element/feature, and not necessarily mechanically, such as when elements or features are embodied in program code. Thus, although the figures depict example arrangements of processing elements, additional intervening elements, devices, features, components, or code may be present in an actual embodiment.

The invention may be described herein in terms of functional and/or logical block components and various processing steps. It should be appreciated that such block components may be realized by any number of hardware, software, and/or firmware components configured to perform the specified functions. For example, an embodiment may employ various integrated circuit components, e.g., memory elements, digital signal processing elements, logic elements, diodes, look-up tables, etc., which may carry out a variety of functions under the control of one or more microprocessors or other control devices. Other embodiments may employ program code, or code in combination with other circuit components.

In accordance with the practices of persons skilled in the art of computer programming, the present disclosure may be described herein with reference to symbolic representations of operations that may be performed by various computing components, modules, or devices. Such operations may be referred to as being computer-executed, computerized, software-implemented, or computer-implemented. It will be appreciated that operations that can be symbolically represented include the manipulation by the various microprocessor devices of electrical signals representing data bits at memory locations in the system memory, as well as other processing of signals. The memory locations where data bits are maintained are physical locations that have particular electrical, magnetic, optical, or organic properties corresponding to the data bits.

As non-limiting examples unless specifically indicated, any database or data store described herein may comprise a local database, online database, desktop database, server-side database, relational database, hierarchical database, network database, object database, object-relational database, associative database, concept-oriented database, entity-attribute-value database, multi-dimensional database, semi-structured database, star schema database, XML database, file, collection of files, spreadsheet, or other means of data storage located on a computer, client, server, or any other storage device known in the art or developed in the future. File systems for file or database storage may be any file system, including without limitation disk or shared disk, flash, tape, database, transactional, and network file systems, using UNIX, Linux, Mac OS X, Windows FAT or NTFS, FreeBSD, or any other operating system.

The various aspects of the invention will be described in connection with configuring systems and devices to detect and classify sympathetic and parasympathetic activity from heartbeat data. That is because the features and advantages that arise due to the invention are well suited to this purpose. However, it should be appreciated that the invention is applicable to other procedures and to achieve other objectives as well.

The systems and methods disclosed herein overcome the drawbacks of known approaches to assessing the influence of the ANS on the subject's heartbeat. In particular, the systems and methods disentangle the influences of the sympathetic branch and the parasympathetic branch by classifying heartbeat events according to two novel indices: the instantaneous sympathetic autonomic index (SAI) and the parasympathetic autonomic index (PAI). These indices, described in detail below, provide separate assessments of the time-varying ANS synergic functions by associating proper combinations of orthonormal Laguerre functions. Such functions may be defined within the heartbeat point-process continuous model, or other modeling techniques such as Kalman filtering, Recursive Least Squares, and Window-based estimation.

Physiological Background and State of the Art

The novelty and advantages of the present systems and methods are best understood based on the following description and related literature pertaining to the ANS, its influence on heartbeat, and previous studies and methodology.

The human body can be understood as a complex multi-feedback physiological system in which spontaneous fluctuations are regulated by the ANS. Either the sympathetic or the parasympathetic system is providing some nervous input to a given tissue at all times. Typically, these two systems have opposing effects on a given tissue (though not all tissues are innervated by nerves of both systems). Either the systems carry sensory (afferent) signals to the brain and spinal cord, or they carry efferent signals from the brain to the target organs. Increasing or decreasing the frequency of the spike trains in the associated neurons of the active system may enhance or inhibit the tissue activity, consequently increasing or decreasing HR. Analysis of HRV may therefore reflect the beat-to-beat regulation of the ANS.

The most widely used methodology to characterize ANS activity is based on a frequency-domain analysis of the HRV. The HRV spectrum has been divided into three main spectral bands: Very Low Frequency (VLF), Low Frequency (LF) and High Frequency (HF). The VLF band is usually <0.05 Hz and it is almost never considered as ANS marker because it is more related to thermal regulation. The LF rhythm (centered in 0.1 Hz) is mainly due to the arterial baroreceptor modulation. It is in fact dramatically affected by the presence of vasomotor noise, which is amplified by the resonance in the baroreflex loop, placed around 0.1 Hz. Current literature suggests that the LF component of the power spectrum is strongly affected by the sympathetic system. A change in the sympathetic gains, in fact, causes a dramatic alteration in this component of the spectrum, leaving the other components almost unchanged.

The HF component (>0.15 Hz), also called the respiratory component, is determined by two concurrent mechanisms. The first is the effect of systemic arterial pressure (SAP) changes mediated by the baroreflex. SAP exhibits respiratory fluctuations caused by intrathoracic and abdominal pressure changes (mechanical effect) and by the lung stretch receptor reflex working on resistance (neurogenic effect). The fluctuations systematically stimulate the baroreflex at the respiratory period. At this frequency, however, the baroreflex works entirely through its strong and fast vagal component, whereas the sympathetic component is almost completely damped out because of its low-pass filtering dynamic.

The second mechanism, showing the direct effect of the lung stretch receptor reflex on heart period, is also mediated by the vagus. A common viewpoint is that the HF peak can be considered as an index of vagal activity. However, the HF peak is modulated by all factors affecting the input to baroreflex and the lung stretch reflex, such as the depth and frequency of breathing, venous compliances in the thoracic and abdominal cavity, posture changes, etc. Further, the HF peak depends strongly on the sensitivity of the cardiac pacemaker to efferent activity. Hence, in different subjects and/or under different breathing conditions, the HF spectral component may be largely different even in the presence of an equivalent vagal gain.

Responsive to the ambiguity between the LF and HF indices, one approach to analyzing the HRV spectrum proposed the ratio of the LF power to the HF power of HR variability as an index of sympatho-vagal balance. Despite commonly accepted definitions of the frequency bands, several pharmacological studies (e.g., selective autonomic blockade) confirmed that components above 0.15 Hz are due to vagal activity only. However, a strong contribution of the HF power modulation is due to the modulation of HR due to respiratory activity (RSA). Besides, changes below 0.15 Hz are mediated by both cardiac vagal and sympathetic nerves. In addition, changes in the LF power of HR variability could also reflect ABP fluctuations, which may cause HR fluctuations through the baroreflex. Clearly, the components of ANS influence attributable to sympathetic and parasympathetic activity remained entangled.

Several more sophisticated methods have been recently proposed to improve the ANS characterization. One method is to quantify the ANS activity using a blind source separation technique of HR and ABP variability, as well as HR and QT waves interval variability. Another method introduced a principal dynamic mode analysis of HR variability to separately characterize the sympathetic and the parasympathetic activity. More recently, another method derived ANS indices based on a multisignal analysis of the R-R variability by processing the HR, ABP, and the instantaneous lung volume.

Present Methodology

The present model may efficiently identify and differentiate the sympathetic and the parasympathetic activity, even in an instantaneous way, based on the use of the Laguerre functions (a.k.a. Laguerre polynomials), which may be applied within a point process framework. The employment of the point process statistics, in fact, would provide several advantages. From the event-related structure of the R-waves, the point-process approach provides instantaneous estimates of heart rate variance and R-R interval variance to accompany instantaneous estimates of heart rate and mean R-R interval. In addition, the present methods assess the model goodness-of-fit, i.e., how well a given model describes the observed R-R interval series as part of its standard analysis framework. A physiologically reasonable history-dependent inverse Gaussian (HDIG) probability function may be used to estimate the time-varying parameters of the model, such as with a local maximum likelihood algorithm. The system may model the mean of the HDIG as a simple linear autoregressive (AR) function of the previous R-R intervals. A crucial role in the sympathetic and parasympathetic identification is given by Laguerre expansion of the AR kernels, as described further below. Alternatively, the HDIG can be replaced with a simple history-dependent Gaussian distribution, a history-dependent log-normal distribution or any other suitable probability distribution. Notwithstanding the advantages of the point-process framework, simpler alternative methods can be used in applications where the simplicity and/or efficiency of implementation outweighs the increased accuracy of the point-process framework.

Referring to FIG. 1, a device 100 performing the present analytical methods may receive an input signal 102 containing typical recorded heartbeat data of a subject. The device 100 may process the input signal through three main stages, which may be defined by modules containing the program instructions for performing the analysis: an acquisition and detection module 104 may identify one or more sets of heartbeat events (e.g., R-waves in an ECG) in the input signal; an index calculation module 106 may determine the sympathetic and parasympathetic activity levels in the heartbeat events; and, an autonomic assessment module 108 may evaluate the activity levels for indicators of certain conditions, which indicators may be augmented with classification modules that are specific to particular applications or conditions. The present methods yield important monitoring and detection improvements in each of these three stages.

The acquisition and detection module 104 may include a subject modeling module 114 and a reference modeling module 116. The subject modeling module may model the mean heart rate in the input signal 102 as a function of linear derivative terms of past R-R intervals, along with the Laguerre expansion thereof in a point-process framework. It will be understood that the below exemplary equations constitute a combination of the Laguerre functions; in other embodiments, the Laguerre functions may be nonlinearly combined and assigned selectively to each of the two branches. Compared with nonlinear transformations, such linear transformations may ease computational cost and simplify implementation of the systems and methods disclosed herein in portable or wearable devices, which have limited computational power and/or battery life.

Given a set of heartbeat events of the subject (e.g., the set $\{u_j\}$, j=1 to J, of R-waves from an ECG), let $RR_j = u_j - u_{j-1} > 0$ denote the $j^{th}$ R-R interval, or equivalently, the wait time until the next R-wave event. The subject modeling module 114 may model the mean heart rate $\mu_{RR}(t, \mathcal{H}_t, \xi(t))$, with respect to the separate influence of the sympathetic and parasympathetic systems, using the modeling equation:

$$\mu_{RR}(t, \mathcal{H}_t, \xi(t)) = RR_{\tilde{N}(t)} + g_0(t) + \underbrace{\sum_{j=0}^{P_{symp}} g_1(j, t) l_j(t)}_{Sympathetic} + \underbrace{\sum_{j=P_{symp}+1}^{P_{parsymp}} g_1(j, t) l_j(t)}_{Parasympathetic}$$

where $j = \tilde{N}(t)$ denotes the index of the previous R-wave event that occurred before time t, $\xi(t)$ is the vector of the time-varying parameters, $\mathcal{H}_t = (u_j, RR_j, RR_{j-1}, \ldots, RR_{j-M+1})$, and the Laguerre expansion of the R-R intervals, in both the sympathetic component and the parasympathetic component of the modeling equation, is determined by:

$$l_j(t) = \sum_{n=1}^{\tilde{N}(t)} \phi_j(n)\left(RR_{\tilde{N}(t)-n} - RR_{\tilde{N}(t)-n-1}\right),$$

with the $i^{th}$-order discrete time orthonormal Laguerre function $\phi_i(n)$ determined by:

$$\varphi_i(n) = \alpha^{\frac{n-i}{2}}(1-\alpha)^{\frac{1}{2}} \sum_{j=0}^{i} (-1)^j \binom{k}{j}\binom{i}{j} \alpha^{i-j}(1-\alpha)^j$$

where (n≥0) and α is the discrete-time Laguerre parameter.

The coefficients $g_0$ and $\{g_1(i)\}$ correspond to the time-varying zero- and first-order autoregressive (AR) coefficients, respectively. This model of the mean heart rate can be interpreted as a discrete AR series with long-term memory. The corresponding AR model with long-term memory becomes:

$$\mu_{RR}(t, \mathcal{H}_t, \xi(t)) = RR_{\tilde{N}(t)} + \gamma_0 + \sum_{i=1}^{\infty} \gamma_1(i, t)\left(RR_{\tilde{N}(t)-i+1} - RR_{\tilde{N}(t)-i}\right)$$

where $\gamma_0$ and $\{\gamma_1(i, t)\}$ represent the AR coefficients defined for each time sample as $$\gamma_0 = g_0$$

$$\gamma_1(i) = \sum_{m=0}^{P} g_1(m)\phi_m(i)$$

In some embodiments, the subject modeling module 114 may receive the base functions attributed to either the sympathetic or the parasympathetic activity from the reference modeling module 116. The reference modeling module 116 may receive or obtain (i.e., from device 100 memory) a reference heartbeat dataset 110 containing reference mean heart rate data that corresponds to the above modeling equation. This reference heartbeat dataset 110 may establish the combinations and structures of the sympathetic and parasympathetic base functions for a set of candidate models. The reference heartbeat data may be pre-modeled, such that the reference heartbeat dataset 110 may be "universally" applied to any potential subject. Alternatively, the reference heartbeat data may be modeled by the reference modeling module 116 in order to calibrate the system for processing the subject's input signal. The subject modeling module 114 and reference modeling module 116 may exchange data for purposes of comparing the subject heartbeat events to the candidate models and determining the best-matching base functions. A match establishes the modeling structure of the coefficient $g_1$ for the sympathetic and parasympathetic base functions, notated as ($g_{1s}$, $g_{1p}$). In an exemplary approach to matching the frequency response of the Laguerre filters with the frequency response of the sympathetic and the parasympathetic systems, the sympathetic and parasympathetic summary ranges may be set to $P_{Symp}=1$ and $P_{ParSymp}=8$ These numbers are the result of physiological and theoretical considerations. The sympathetic nervous system, in fact, has slow-varying dynamics whose upper frequency band limit is 0.15 Hz. Accordingly, Laguerre bases $l_j$ should be limited to $j=0^{th}$ and $j=1^{st}$ orders. On the other hand, the parasympathetic nervous system has varying dynamics whose upper frequency band limit is 0.45 Hz. Accordingly, Laguerre bases $l_j$ should be limited to $j=8^{th}$ order.

Whether the SAI and PAI indices are embedded in a point-process framework, the mean heart rate can be defined in an instantanous fashion, and the system may obtain instantaneous R-R estimates at a very fine timescale (e.g., millisecond scale) that requires no interpolation between the arrival times of two beats.

Figure 2:
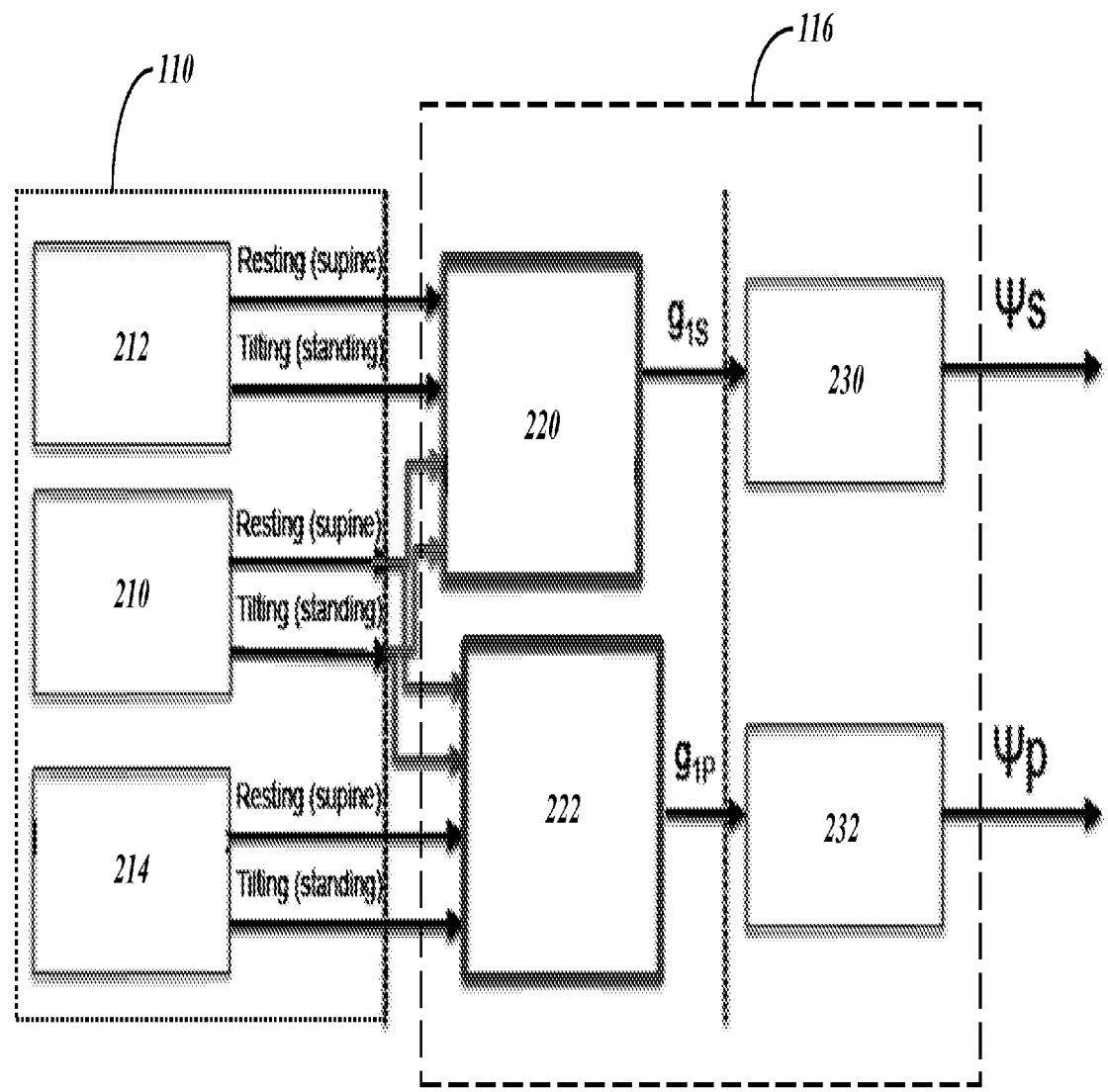
FIG. 2 is a diagram of an embodiment of a reference modeling module operating on a reference heartbeat dataset in accordance with the present disclosure.

FIG. 2 illustrates the reference modeling module 116 in further detail. Once the modeling structure ($g_{1s}$, $g_{1p}$) is determined, the reference modeling module 116 may use the modeling structure to evaluate a four-stage model of the reference heartbeat dataset 110 and produce the actual values of $g_{1s}$ and $g_{1p}$. In particular, the reference heartbeat dataset 110 may include, for each candidate model, data subsets including total autonomic modulation data 210, sympathetic activity only data 212, and parasympathetic activity only data 214. Each data subset may include reference data obtained from a subject, which may be the actual subject to be monitored or may be a reference subject or set of subjects (e.g., one or more non-smoking adults of similar age and weight and with no history of cardiopulmonary disease), in one or both of a supine position and in a standing position. The reference data collection process may mirror the testing of the subject being monitored; examples are given below for obtaining the data (e.g., via one or more ECG leads) while moving the subject between supine and standing states and administering autonomic blocking agents.

The four-stage model may include a sympathetic data modeler 220 and a parasympathetic data modeler 222. The sympathetic data modeler 220 may process the total autonomic modulation data 210 and the sympathetic activity only data 212 together, producing the value(s) of $g_{1s}$. The parasympathetic data modeler 222 may process the total autonomic modulation data 210 and the parasympathetic activity only data 214 together, producing the value(s) of $g_{1p}$. In some embodiments, estimates of $g_{1p}$ and $g_{1s}$ may be obtained through maximum local log-likelihood procedures. For example, a Newton-Raphson procedure may be used to maximize the local log-likelihood function. Because there is significant overlap between adjacent local likelihood intervals in time, the Newton-Raphson procedure may be initiated at time t with the previous local maximum-likelihood estimate at time t−Δ, where Δ defines the time interval shift to compute the next parameter update.

The results of the sympathetic data modeler 220 and the parasympathetic data modeler 222 may be delivered to one or more multiple regression modelers 230, 232. In one embodiment, a multiple regression modeler may operate on both $g_{1s}$ and $g_{1p}$, but in the illustrated embodiment $g_{1s}$ is delivered to a first multiple regression modeler 230 and $g_{1p}$ is delivered to a second multiple regression modeler 232. The multiple regression modelers 230, 232 may produce the disentangling coefficients $\Psi_s$, $\Psi_p$ by minimizing the least square error between the actual regression output and the reference function associated to the sympathetic/parasympathetic nervous system (i.e., the relevant increase/decrease of activity while in upright position after tilt). In one embodiment, the disentangling coefficients $\Psi_s$, $\Psi_p$ may be vectors or arrays having a plurality of elements. The number and values of the elements for each coefficient may be determined from analysis of an instant data set, such as the subject data or reference data, or may be predetermined from earlier analysis of other datasets. Advantageously, these parameters may be selected to provide the most favorable discrimination accuracy of autonomic states and disentangling of sympathetic and parasympathetic components.

In a particular embodiment, the coefficient $\Psi_s$ may have three elements:

$$\Psi_s = \{a_0, a_1, a_2\}$$

and the coefficient $\Psi_p$ may have eight elements:

$$\Psi_p = \{b_0, b_1, b_2, b_3, b_4, b_5, b_6, b_7\}$$

These numbers represent the weighted sum of Laguerre representation of the heartbeat data under investigation. This combination may be performed with fewer or more elements, while preserving the time and frequency domain properties of the output. In a physiological parallelism, these coefficients model the way the parasympathetic and sympathetic activities are mapped in the R-R variability, noninvasively detected through acquisition methods described above. Potentially optimal sets of values for the elements of the coefficients is given below in the described experimental results (see Tables I-VI). Other vector dimensions and element values may also be suitable, or even superior, to the exemplary values depending on the characteristics and needs of the subject and the parameters of the system's operation.

Within such embodiments, the inventors have envisaged different coefficient values or modification of the SAI/PAI definition of elements, when dealing with estimates to be performed in any case of pathological subjects, or healthy subjects of any age (premature newborns, newborns, infants, teenagers, adults, elderly). They also have envisaged different novel (NEW(i)) criteria to handle information from the blockade/tilt procedure, and estimate $\Psi_s$ and $\Psi_p$ based on the main principles that: (a) parasympathetic suppression (or sympathetic activation/prevalence during tilt)→sympathetic regressors; and (b) sympathetic suppression (or parasympathetic activation/prevalence during tilt)→parasympathetic regressors. Those criteria are:

NEW(0): $\Psi_s$ and $\Psi_p$ are obtained through personalized regression analysis. An exemplary subject's recording while in autonomic blockade/rest-tilt condition is used to obtain personalized coefficient values. These values may be used to perform SAI/PAI estimates of using that specific subject data.

NEW(1): $\Psi_s$ and $\Psi_p$ are obtained through personalized regression analysis. More than one exemplary subject's recordings while in autonomic blockade/rest-tilt conditions are used to obtain personalized coefficient values. These values may be used to perform SAI/PAI estimates of using that specific subject data.

NEW(2): $\Psi_s$ and $\Psi_p$ are obtained through regression analysis performed on a training set. Recordings from a number of subjects, monitored while performing several rest-tilt tests (e.g., stand up tests, and a slow-tilting test, and a fast-tilting test), are used to obtain coefficient values. These values may be used to perform SAI/PAI estimates on data gathered from a new subject who does not belong to the training set.

NEW(3): $\Psi_s$ and $\Psi_p$ are obtained through regression analysis performed on a training set. Recordings from a number of subjects, monitored while performing one specific rest-tilt test (e.g., a stand up test, or a slow-tilting test, or a fast-tilting test), are used to obtain coefficient values. These values may be used to perform SAI/PAI estimates on data gathered from a new subject who does not belong to the training set.

NEW(4): $\Psi_s$ and $\Psi_p$ are obtained through regression analysis performed on a training set. Recordings from a number of subjects, monitored while undergoing autonomic blockade procedure and concomitant tilt tests, are used to obtain coefficient values. Data from parasympathetic suppression are used to estimate sympathetic regressors, i.e., to be used for the SAI index. Data from sympathetic suppression are used to estimate parasympathetic regressors, i.e., to be used for the PAI index. These values may be used to perform SAI/PAI estimates on data gathered from a new subject who does not belong to the training set. Of note, the parameters obtained with this strategy are the current point of reference for the modules described below.

An extensive study of a proposed embodiment has been performed in order to provide coefficient reference values, with resulting choice of reference mean and associated standard deviation for the coefficients as follows:

$\Psi_s = \{39.2343, 10.1963, -5.9242\}$; and $\Psi_p = \{28.4875, 17.3627, 5.8798, 12.0628, 5.6408, 7.0664, -5.6779\}$;

with the following standard deviation:

$std(\Psi_s) = \{17, 10, 6.1\}$; and $std(\Psi_p) = \{11.5, 8.5, 8, 7.3, 6.8, 4.9, 5.2, 5.9\}$.

Specific coefficients, used to obtain results in Table I, II, and III of this document, are listed in the tables "SYMPATHETIC COEFFICIENT" and "PARASYMPATHETIC COEFFICIENT" below.

technique; thus, the model-defined parameters can be updated in real-time using any suitable recursive parameter estimation technique. The heartbeat detection and correction method is very flexible and allows for consideration of any kind of signal containing information about the heartbeat. Thus, the systems and methods may use any heart rate source (e.g., photoplethysmography, ECG, cameras), not limited to cardiac ventricular electrical activity (i.e., ECG), to separate sympathetic nervous activity (SNA) and parasympathetic nervous activity (PNA). Advantageously, the implemented routines are able to recognize missing, spurious, misdetected, and irregular heartbeats with remarkable accuracy even in scenarios that require discerning very small time resolution errors, such as at millisecond scales. The correction procedure provides accurate estimates of the replacement time of an unobserved beat, with an error below 15 ms, outperforming other existing methods of estimating the time of missing beats.

In an exemplary application, the detection and correction method may provide data to an arrythmia alarm. Only a small number of devices are available with modules providing lethal and nonlethal arrhythmia alarms; these are based on multi-lead ECG morphological features, and thus are very sensitive to ECG noise. An alarm system implementing the present methods may identify or predict an arrhythmia based on only the time distance within beats, independently from relevant sources of ECG noise. Thus, the alarm system may process an ECG signal with improved efficiency and accuracy, and may be configured to process any other type of signal carrying heart beat event information (e.g., photopletimographic pulse signal, video camera signal, ballistogram, ultra wideband cardiogram, and the like).

Referring again to FIG. 1, the point-process framework of the acquisition and beat detection module 104 is able to obtain the mean instantaneous heart rate signal from the input signal, as well as instantaneous time and frequency-domain HRV characterization. In addition, the framework may output the corresponding modeling structure ($g_{1s}$, $g_{1p}$) and the disentangling coefficients $\Psi_s$, $\Psi_p$ to the index calculation module 106. The index calculation module 106 may process the received data to produce corresponding values in a Sympathetic Activity Index (SAI) and a Parasympathetic Activity Index (PAI).

| SYMPATHETIC COEFFICIENT | | | |
|---|---|---|---|
| | $a_0$ | $a_1$ | $a_2$ |
| NEW(0): | 13.4670 | 9.5615 | −5.4347 |
| NEW(1): | 10.4879 | −0.0964 | 3.8631 |
| NEW(2): | 12.7621 | 12.3300 | −0.8704 |
| NEW(3): | 46.4851 | 27.5524 | −12.4655 |
| NEW(4): | 39.2343 | 10.1963 | −5.9242 |

| PARASYMPATHETIC COEFFICIENT | | | | | | | | |
|---|---|---|---|---|---|---|---|---|
| | $b_0$ | $b_1$ | $b_2$ | $b_3$ | $b_4$ | $b_5$ | $b_6$ | $b_7$ |
| NEW(0): | 6.6066 | −1.5879 | 5.0206 | 4.3343 | 3.4950 | 1.0075 | 3.0551 | 0.6538 |
| NEW(1): | 6.8147 | −3.6488 | 3.7703 | 4.2896 | −4.7193 | −3.2025 | 4.8458 | 2.2086 |
| NEW(2): | 6.2444 | −7.6437 | 3.2773 | 1.9761 | 2.9275 | 0.7848 | −0.7313 | 4.5324 |
| NEW(3): | 26.7460 | −20.3547 | 21.9453 | 19.6561 | −9.8526 | −9.6707 | 8.0036 | −10.2943 |
| NEW(4): | 28.4875 | −17.3627 | 5.8798 | 12.0628 | 5.6408 | −7.0664 | −5.6779 | −3.9474 |

The model parametric structure allows for appropriate insertion of parameters according to the chosen estimation The index calculation module 106 may include a time-varying estimation module 140 and a SAI-PAI generation module 142. The time-varying estimation module 140 may perform an iterative estimation along a period of time of the novel SAI-PAI indices by generating, from the values of $g_{1s}$ and $g_{1p}$ output by the acquisition and beat detection module 104, time-varying values of $g_{1s}$ and $g_{1p}$ at each iteration using any suitable signal processing method. For example, a simple Kalman filtering method can be used to track the SAI-PAI dynamics (i.e., the values of $g_{1s}$ and $g_{1p}$) at each heartbeat, or an instantaneous estimation (i.e., at each moment in time) can be performed using the point-process modeling. Traditional recursive least-square and window-based signal processing methods can also be applied.

The time-varying values of $g_{1s}$ and $g_{1p}$ and the disentangling coefficients $\Psi_s$, $\Psi_p$ may be received by the SAI-PAI generation module 142 and combined to yield the SAI and PAI indices for the subject input signal 102. The SAI and PAI may be expressed, in one embodiment, in the following matrix form:

$$SAI(t, \mathcal{H}_t, \xi(t)) = \Psi_{S_0} + \sum_{j=1}^{N_1} \Psi_{S_j} g_1(j-1, t)$$

$$PAI(t, \mathcal{H}_t, \xi(t)) = \Psi_{P_0} + \sum_{j=1}^{N_2} \Psi_{P_j} g_1(j + (p_s + 1), t)$$

with $N_1 = p_s + 1$ and $N_2 = p_p - (p_s + 1)$, and $\Psi_{sj}$ and $\Psi_{Pj}$ corresponding to the $j^{th}$ coefficient of the above-described $\Psi_s$ and $\Psi_p$ vectors. The SAI and PAI may be calculated for each interval in the time period, for a subset of the intervals, or for the entire time period, as is suitable for the desired assessment.

The SAI and PAI provide, in a mathematical framework, specific and effective (at least for identification and assessment) markers associated with the independent dynamics of the two autonomic branches. Moreover, the SAI and PAI can be obtained exclusively from the heartbeat, universally applied to a wide range of subjects, and specifically tailored to the subject. The system combines a set of orthonormal filters, represented by the Laguerre polynomials, in a unique fashion to provide appropriate and separate frequency responses for sympathetic and parasympathetic cardiac tone. The parameters of each combination of sympathetic and parasympathetic base functions may be identified by obtaining the reference heartbeat data from reference patients under separate sympathetic and parasympathetic blockades. This data is processed using the above equations and modelers, which construct an underlying probabilistic model able to indicate with precision the degree of probability of having the next heartbeat at each moment in time given the previously observed heartbeats. The flexibility of the system is improved by using a combinatorial formula that is based on time-varying coefficients which can be identified with any of several suitable identification systems.

In particular, the SAI and PAI may be generated from a procedure for tuning the combination parameters by appropriately fitting the mathematical model to specific datasets where either one of the two autonomic branches is blocked. Additionally, the SAI and PAI may be determined from pre-stored decisional thresholds that are applied to all subjects, and have been demonstrated to work on a wide range of experimental recordings, with high robustness to noise and ability to cope with inter-subject variability. Finally, since the SAI-PAI model may be defined in real-time and is updated recursively, the system may process decisional trees in real-time using only short-time past information, and then can finalize the outcome within at maximum three beats in the future. The system may be used for processing any heartbeat interval series and consequent application for any kind of HRV analysis.

The SAI and PAI values may be delivered to the autonomic assessment module 108, which may specifically or comprehensively assess the sympathetic and parasympathetic activity levels indicated by the SAI and PAI values. The framework has also been proved successful in significantly reducing inter-subject variability. These results have been confirmed by applying and comparing the present approach on hundreds of healthy and unhealthy subjects in different physiological and environmental settings. Specific assessments may be assessments of the SAI and PAI values in light of particular applications that seek to detect activity of a certain nature. Six exemplary application modules are described herein, and are not intended to be limiting. The empirical performance of the six designed modules provide compelling evidence for application of the system in a wide range of clinical and non-clinical fields. One or more of the modules may be implemented on a suitable device that is otherwise configured to perform the present processes.

In one embodiment, a statistical comparator module 158 may include program instructions and associated data for performing a statistical comparison of the SAI and PAI values to existing standard measures such as the LF, HF and LF/HF powers. Such a statistical comparison is demonstrated in the experiment described below, and indicates enhancements (in some instance by a factor of 2!) of the statistical power of the SAI and PAI values when compared with standard measures. The statistical comparator module 158 may additionally train itself or the system at large to identify signatures of autonomic dysfunction in the patient by comparing SAI and PAI values to previous SAI and PAI values and/or current or previous standard measures that have known signatures.

In one embodiment, a clinical monitor module 160 may include program instructions and associated data for online monitoring of heart rate variability indices, counting of arrhythmic events, and cardiovascular instability. Additionally or alternatively, the clinical monitor module 160 may evaluate the instantaneous HRV indices to detect and predict hypotensive episodes in cardiopathic subjects admitted to a clinical setting (e.g., ICU). Additionally or alternatively, the clinical monitor module 160 may use the HRV indices to track drug effects on cardiovascular functioning, such as during anesthesia, and to disentangle these effects from the nociceptive autonomic component elicited from painful stimuli occurring during surgical and non-surgical procedures. The clinical monitor module 160 relies on the separate sympathetic and parasympathetic assessment to provide a more accurate dynamic signature of nociception, generally associated with specific dynamics of the sympathetic autonomic branch. The module can be tested by pursuing specific protocols where anesthetic drugs and painful stimuli are administered in controlled doses and at different strengths.

In one embodiment, a sleep monitor module 162 may include program instructions and associated data for monitoring heart rate and heartbeat events during sleep. The sleep monitor module 162 may classify events and/or perform sleep scoring based on the generated HRV indices, including a linear and/or nonlinear combination of the SAI-PAI indices, and by feeding such features to supervised or unsupervised learning algorithms. In the same fashion as described in previous work of the inventors, the present approach is able to identify fast dynamics that allow for sleep characterization at higher time resolution than traditional methods and to track fast changes that indicate transitions from deep to light sleep or wake, as well as onsets of brief cardio respiratory arousals and transitions. Thanks to the inclusion of the SAI and PAI indices, identification of fast dynamics is expected to predict these transient phenomena and provide an accurate classification, while also tracking autonomic changes and transitions between stages in an on-line fashion. These features may provide a significant improvement over previous similar approaches and a solid base for building real-time sleep monitoring and bio-feedback devices.

In one embodiment, a stress monitor module 164 may include program instructions and associated data for classifying heartbeat data according to states of arousal (i.e., relaxation and stress). The stress monitor module 164 may apply suitable stress and/or relaxation protocols, such as emotional elicitation and Strupp tests, to system-processed data to determine a stress state or stress level of the subject, both derived by feeding information from a linear and/or nonlinear combination of the SAI-PAI indices (in addition to any other discretional set of features) to supervised or unsupervised learning algorithms. The stress monitor module 164 thus operates in a similar fashion to the sleep monitor module 162, in some embodiments using classification procedures described in the inventors' previous work in order to define a univocal relationship between the combinational values and specific sectors along the arousal axis.

In one embodiment, a physical activity monitor module 166 may include program instructions and associated data for evaluating heartbeat data collected during exercise and/or recovery from exercise, and in different cardiovascular conditions (e.g., cycling and car driving). The physical activity monitor module may serve to evaluate the subject's exercise regime, which can be directly derived from a linear and/or nonlinear combination of the SAI-PAI indices. Indices corresponding to specific levels of exercise and physiological states related to them can be derived by feeding information from a linear and/or nonlinear combination of the SAI-PAI indices (in addition to any other discretional set of features) to supervised or unsupervised learning algorithms.

Figure 3:
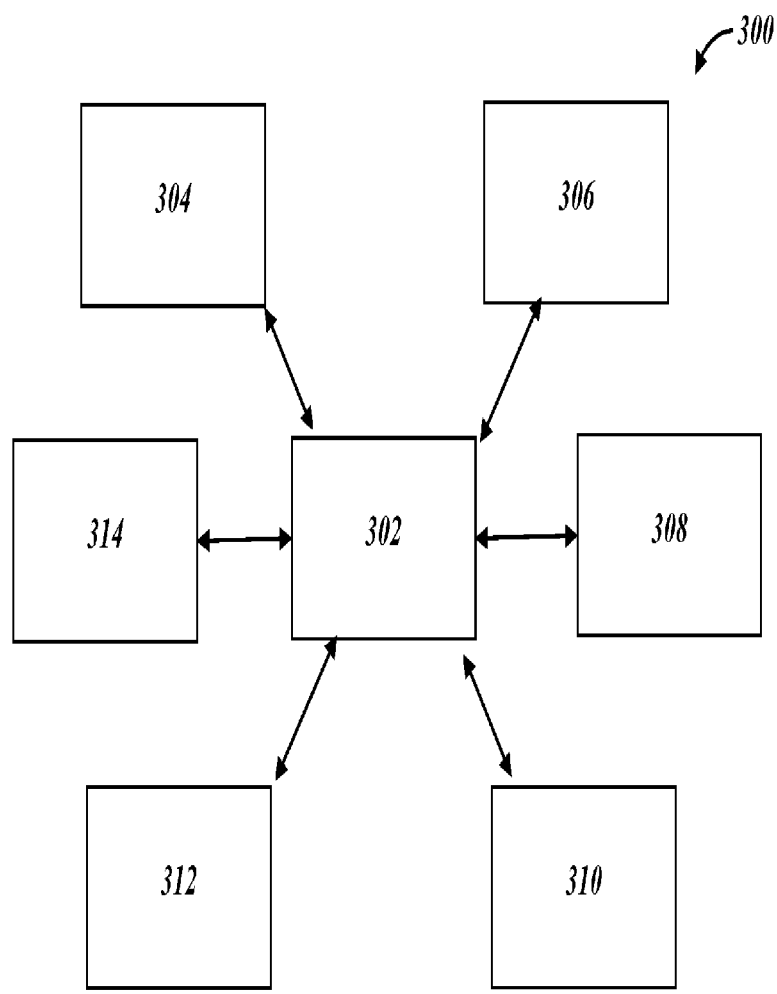
FIG. 3 is a diagram of a system configured to implement the data acquisition, processing, and storage methods of the present disclosure.

In one embodiment, an emotional state monitor module 168 may include program instructions and associated data for classifying heartbeat data according to states of emotion, based on states of arousal (i.e., relaxation and stress) or valence (i.e. positive or negative). The emotional state monitor module 168 may characterize and separate different emotional states in real-time during emotional elicitation, such as during IAPS tests. The emotional state monitor module 168 may operate in a similar fashion to the classification procedures described in the inventors' previous work, in order to define a univocal relationship between the combinational values and specific sectors of the valence-arousal plane, or may be using other supervised or unsupervised learning algorithms. In one embodiment, the emotional state monitor module 168 may configure the autonomic assessment module to classify the recorded data in one of four states—happy, angry, relaxed, and sad—selected according to the arousal-valence plane. The classification accuracy of the system is estimated to outperform results obtained by previous systems using this classification scheme, such as those previously described by the inventors, let alone any other known system As explained above, a computerized system may implement the present invention. A computing device for the system may be a standalone computer having a processor, memory, network connection, and other computer resources as needed to perform the present methods and implement the present hardware and software devices. A computing device may additionally or alternatively be a group of computers in electronic communication with each other; the computers may be controlled by the same or a different entity. Referring to FIG. 3, a system 300 for performing the modeling, estimation, and assessment methods described above may include the computing device 302 and a plurality of modules for performing one or more steps of the methods. The modules may be hardware or software-based processing modules located within the computing device 302, in close physical vicinity to the computing device 302, or remote from the computing device 302 and implemented as stand-alone computer servers or as components of one or more additional servers. The modules may individually or in combination implement the heartbeat data processing modules described above (e.g., the acquisition and detection module 104, the index calculation module 106, and the autonomic assessment module 108 of FIG. 1). The modules may include, without limitation: a user interface module 304 for providing input/output capabilities between the system 300 and a user; a data retrieval module 306 for obtaining the input signal (e.g., accessing or downloading a stored file containing the input signal data, or accessing a data stream produced by sensors of the system), obtaining or accessing the reference heartbeat dataset(s), or performing other data retrieval functions; a modeling module 308 containing one or more data processing algorithms and performing heartbeat acquisition and data modeling of the input signal against the reference heartbeat dataset(s); an estimation module 310 for generating the SAI and the PAI from the modeled data; one or more assessment modules 312 for analyzing the SAI and PAI comprehensively and/or with respect to specific applications; and a communication module 314 for communicating with other computing devices.

Figure 4:
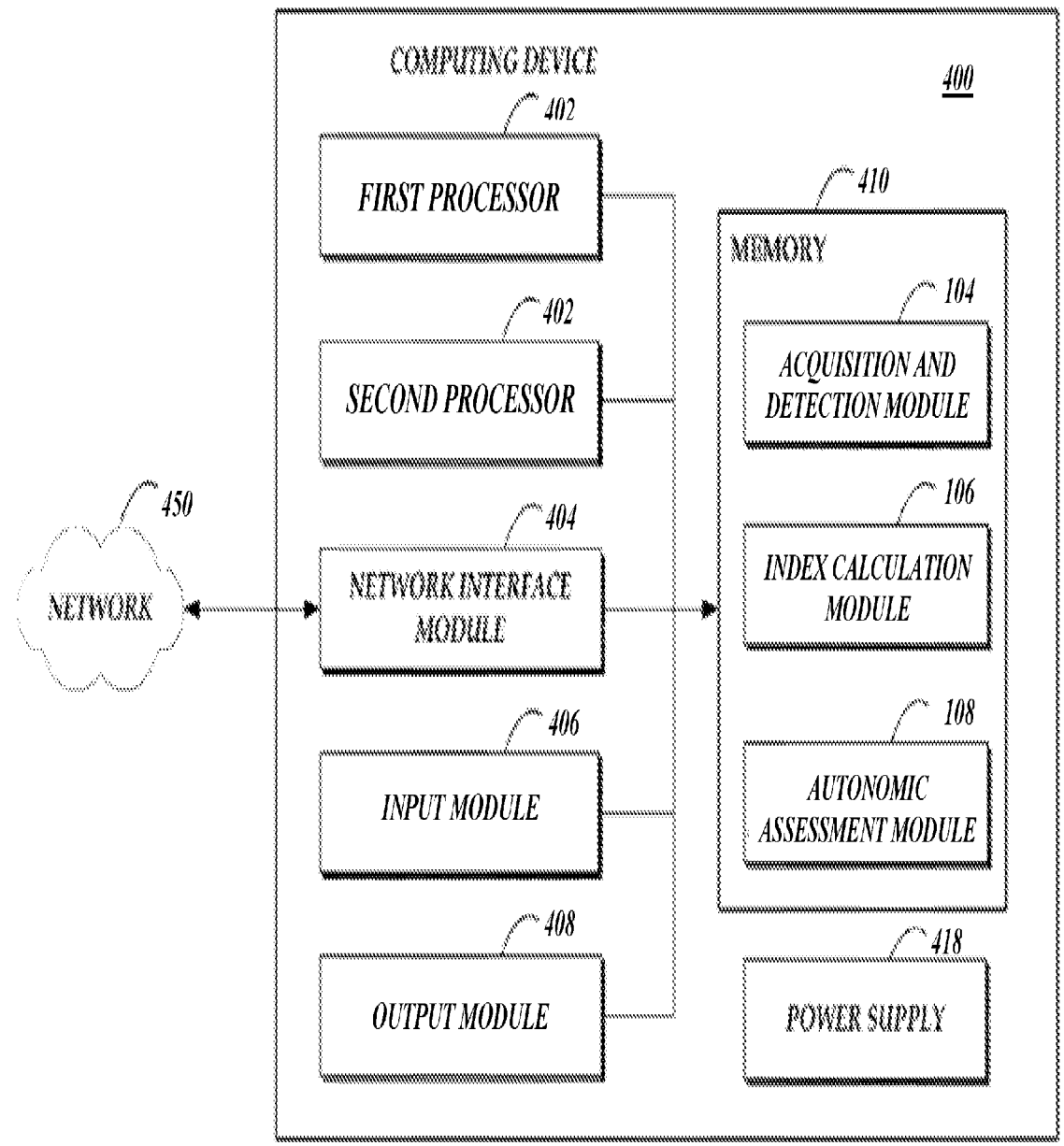
FIG. 4 is a diagram of a device configured to implement the systems and methods of the present disclosure.

FIG. 4 illustrates a computing device 400 that can perform the present heartbeat data analysis processes. The computing device 400 includes at least one processor 402, a network interface module 404, an input module 406, an output module 408, and memory 410, all of which may communicate with one another by way of a communication bus. The computing device 400 may also include a power supply 418, which may provide power to the various components of the computing device 400.

The processors 402 may include one or more microprocessors specially configured to communicate with the memory 410 to implement various software modules and associated program instructions stored therein; such modules may include the acquisition and detection module 104, the index calculation module 106, and the autonomic assessment module 108. The memory 410 generally includes RAM, ROM, flash memory, solid state memory, and/or other persistent or non-transitory computer-readable storage media. The modules 104-108 may be stored as program instructions in memory. When executed by the processor(s) 402, the modules 104-108 may configure the processor(s) 402 to perform the ANS analysis processes described herein. Execution of the modules 104-108 may configure or instruct the processor(s) 402 to access and/or use other modules of the computing device 400, including without limitation: accessing the network interface module 404 or input module 406 to retrieve an input signal or reference heartbeat data; accessing the network interface module 404 to send analyzed data to another device; and accessing the output module 408 to display or otherwise transmit information to a user of the computing device 400.

The network interface module 404 may provide the computing device 400 with connectivity to one or more networks 450, such as a LAN or a wide-area network. The network interface module 404 may additionally or alternatively enable peer-to-peer connectivity directly to other devices, such as via Bluetooth or Wi-Fi Direct. The processor(s) 402 may send instructions and information to, and receive instructions and information from, remote computing devices that also communicate via the network 450. In some embodiments, the network interface module 404 comprises a wireless network interface that provides the computing device 400 with connectivity over one or more wireless networks.

The input module 406 may include one or more input devices, such as a microphone, camera, or touchscreen, and/or one or more interfaces to input devices external to the device 400, such as a keyboard, a biosensor, or a heartbeat data acquisition device (e.g., ECG machine, heart monitor). In some embodiments, the input module 406 may receive the input signal containing the heartbeat data of a subject, and may deliver the input signal to the processor(s) 402 or store the input signal in memory 410. The input module 406 may include any suitable components for converting analog (e.g., acoustic) and/or digital signals into data that is readable by the processor(s) 402, such as piezoelectric transducers, amplifiers, rectifiers, and other signal processing devices.

The output module 408 may be an output device, such as a display screen or a speaker, along with any requisite electronic components for converting a signal of the computing device 400 into a visual or acoustic signal; or, the output module 408 may include interfaces to a display, a speaker, a biometric monitoring system, or another device. The output module 408 may output results of of the heartbeat data analysis performed by the computing device 400, and/or may output prompts for additional information before, during, or after the analysis. The output module 408 may also output alerts related to the heartbeat data and/or status messages (e.g., errors, completion status) related to the processing.

One or more additional input devices such as light sensors, position sensors, biometric sensors (e.g., ECG leads), image capture devices, or the like may be provided with the computing device 400. Such additional input devices are not shown in FIG. 4 so as not to obscure the principles of the present disclosure. In some embodiments, an additional input device may detect the occurrence or non-occurrence of a condition. Information pertaining to such conditions may be provided to the processor 402 to determine whether one or more components of the computing device 400 should be activated or deactivated. In one embodiment, the additional input device includes an image capture device configured with facial recognition capabilities.

The systems and methods of the present disclosure may be implemented in hardware and software components of any suitable device, as described above. In one example, the device may be a heartbeat acquisition device including hardware and software that cooperate to obtain an input signal that is a recording of a subject heartbeat. Further, the heartbeat acquisition device may be combined with sensors and other hardware and software components for acquiring other signals, such as in a comprehensive biometric acquisition system. Hardware modules of the heartbeat acquisition device may include or be integrated with real-time signal acquisition devices (i.e ECG, pulse oximetry, plethismography devices, cameras), and may further include a module for vital signs monitors and alarm systems for clinical and/or non-clinical settings. To the extent the present system is implemented with program instructions, the program instructions may include, or be configured to interface with, software that operates the real-time signal acquisition devices.

In another example, the device may be a user device, such as a desktop computer, a mobile device (e.g., smartphone), or a wearable smart device (e.g., smart watch, bracelet, biosensor-enabled clothing or bandages). Alternatively, the device 100 may be one or more servers with which the user device communicates via wired or wireless network connection. Alternatively, the device 100 may include multiple interconnected devices that cooperate to perform the methods. For example, the acquisition and detection module 104 and the index calculation module 106 may be installed on or operable by a server, and the autonomic assessment module 108 may be installed on or operable by a user device connected to the server and configured to obtain the SAI and PAI, and potentially other data, from the server. The user device may store or access one or more executable applications for assessing the SAI and PAI, such as a sleep scoring application, a stress or exercise tracking application, an emotion identification application, and the like. In another example, the input signal may be acquired by an acquisition device and transmitted to a server, the server may perform the modeling and estimation functions to produce the SAI and PAI, and the server may transmit the SAI and PAI to a user device.

In another example, the systems and methods may be embodied in a distributable (e.g., on physical media or via download) computer program product, which may be installed on a suitable device, as described above, and may configure the device to perform comprehensive automatic analysis of autonomic heartbeat dynamics. The product may, in some embodiments, be used for validation or other analysis of any diagnosis or study pertaining to heart rate and heart rate variability. The product may include program instructions implementing or interfacing with any of the modules described above. Each or all of these modules may either be linked to acquisition modules within a monitoring device (i.e., for real-time analysis and visualization), or they may operate on previously recorded data stored on the device or in a data store accessible by the device.

This written description uses examples to disclose the invention, including the best mode, and also to enable any person skilled in the art to practice the invention, including making and using any devices or systems and performing any incorporated methods. The patentable scope of the invention is defined by the claims and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

Finally, it is expressly contemplated that any of the processes or steps described herein may be combined, eliminated, or reordered. Accordingly, this description is meant to be taken only by way of example, and not to otherwise limit the scope of this invention.

EXAMPLES AND EXPERIMENTAL DATA

The SAI and PAI, as definitions of ANS activity, were compared with the current frequency-based methods in an example study of ECG recordings from 10 healthy subjects during a tilt-table experiment and a selective autonomic blockade. With appropriate choices of the model regressors, this approach can be used to investigate the response characteristics of various ANS sub-systems. In particular, the tilt-table protocol and selective autonomic blockage each have a high presence of non-linearity and non-stationarity in the RR time series. Results from ten RR series recorded during the tilt-table protocol and blockade showed that the proposed methodology, differently than the traditional spectral parameters, appropriately distinguishes changes in the separate ANS branches.

In the tilt-table study, the subjects were five men and five women: age (mean SD) 28.7(1.2) yr, height 172.8(4.0) cm and weight 70.6(4.5) kg. A subject was first placed horizontally in a supine position, with restraints used to secure her at the waist, arms, and hands. The subject was then tilted from the horizontal to the vertical position and returned to the horizontal position. Each subject performed six tilt sessions remaining in each tilt state for 3 min. The protocol lasted 55-75 min (3,300-4,500 s). A single-lead ECG was continuously recorded for each subject during the study, and the R-R intervals were extracted using a curve length-based QRS detection algorithm.

In the selective autonomic blockade study, fourteen male nonsmoking adult volunteers (ages 19-38 yr, median 21 yr) participated. No subject had a history of cardiopulmonary disease. One lead of a surface ECG was recorded. Subjects were instructed to initiate a breath with each tone of a series of auditory cues. The sequence of tones was generated by a computer and recorded on cassette tape for playback during each experiment. The tones were evenly spaced in time at a preset rate of 12 breaths/min to allow the subject to find a comfortable depth of inspiration. Then the program switched to a mode in which the tones were spaced at irregular intervals, but with the same mean rate of 12 breaths/min. Starting from a supine position, the subject was moved to the standing position, and after a minimum of 5 min for hemodynamic equilibration, the calibration procedure and breathing protocol were repeated. These conditions, before any autonomic blockade, are the supine and standing control states, which would comprise the total autonomic modulation data of one candidate in the reference heartbeat dataset described above.

The subject was then returned to the supine position and given either atropine (0.03 mg/kg, n=7) or propranolol (0.2 mg/kg, n=7). After 10 min for equilibration, the above breathing protocol was repeated with the subject supine and then standing. The recorded data in each position would comprise the sympathetic activity only data or the parasympathetic activity only data, depending on the blockade received, of the corresponding candidate in the reference heartbeat dataset described above. The subject was again returned to the supine position and given the other autonomic blocking agent. The supine and standing breathing protocols were repeated under double blockade for all 14 subjects. Because HR control is primarily via the vagus in normal supine humans, the above protocol allowed for an investigation of pure parasympathetic modulation of HR when subjects were in the supine position after propranolol. Further, as sympathetic outflow increases from very low levels when the position is changed from supine to standing, pure sympathetic modulation could be investigated when subjects were in the standing position after atropine.

Figure 5:
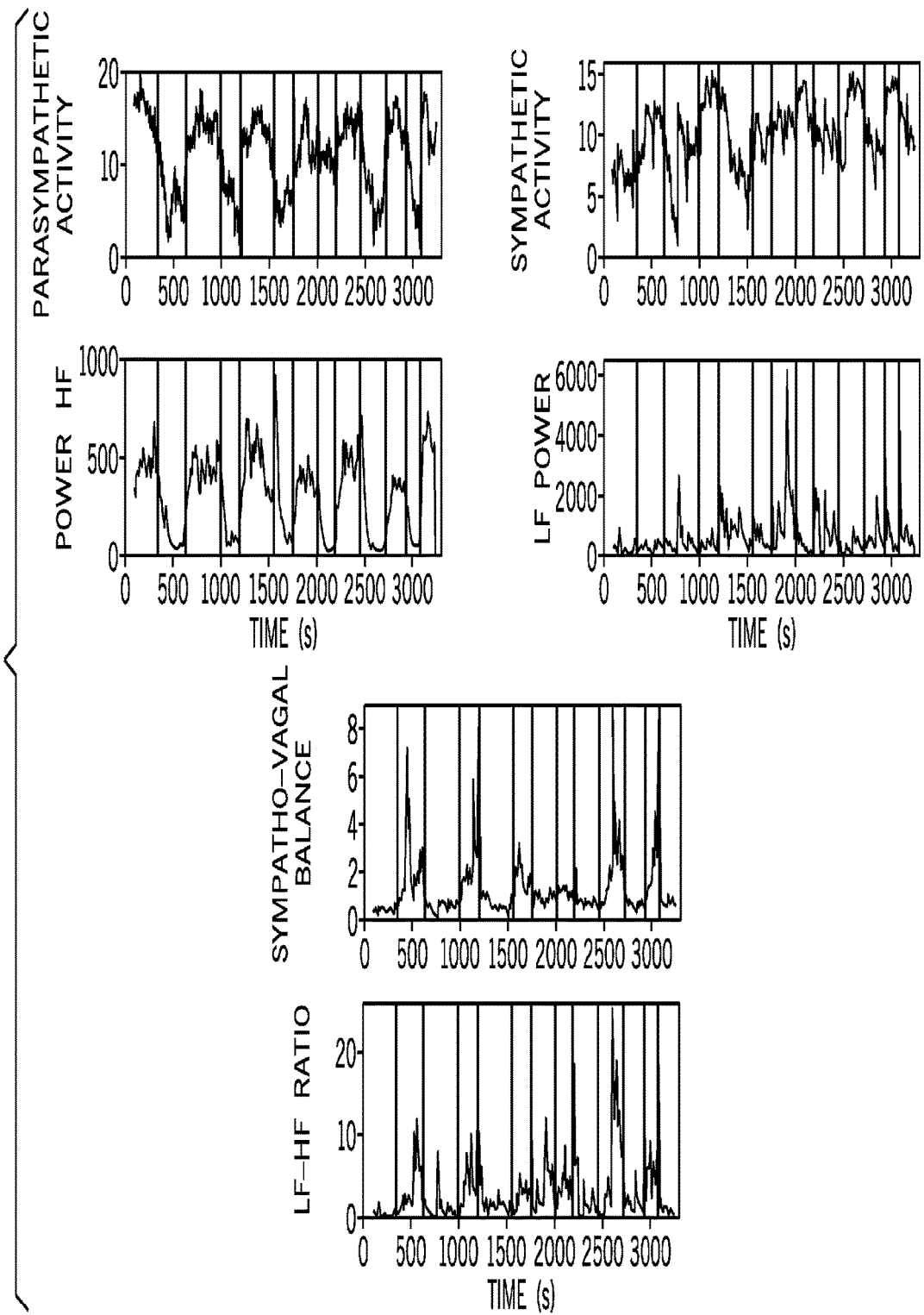
FIG. 5 is a graph representing experimental results of the system of FIG. 1 processing heartbeat data of a representative subject of the experiment.
Figure 6:
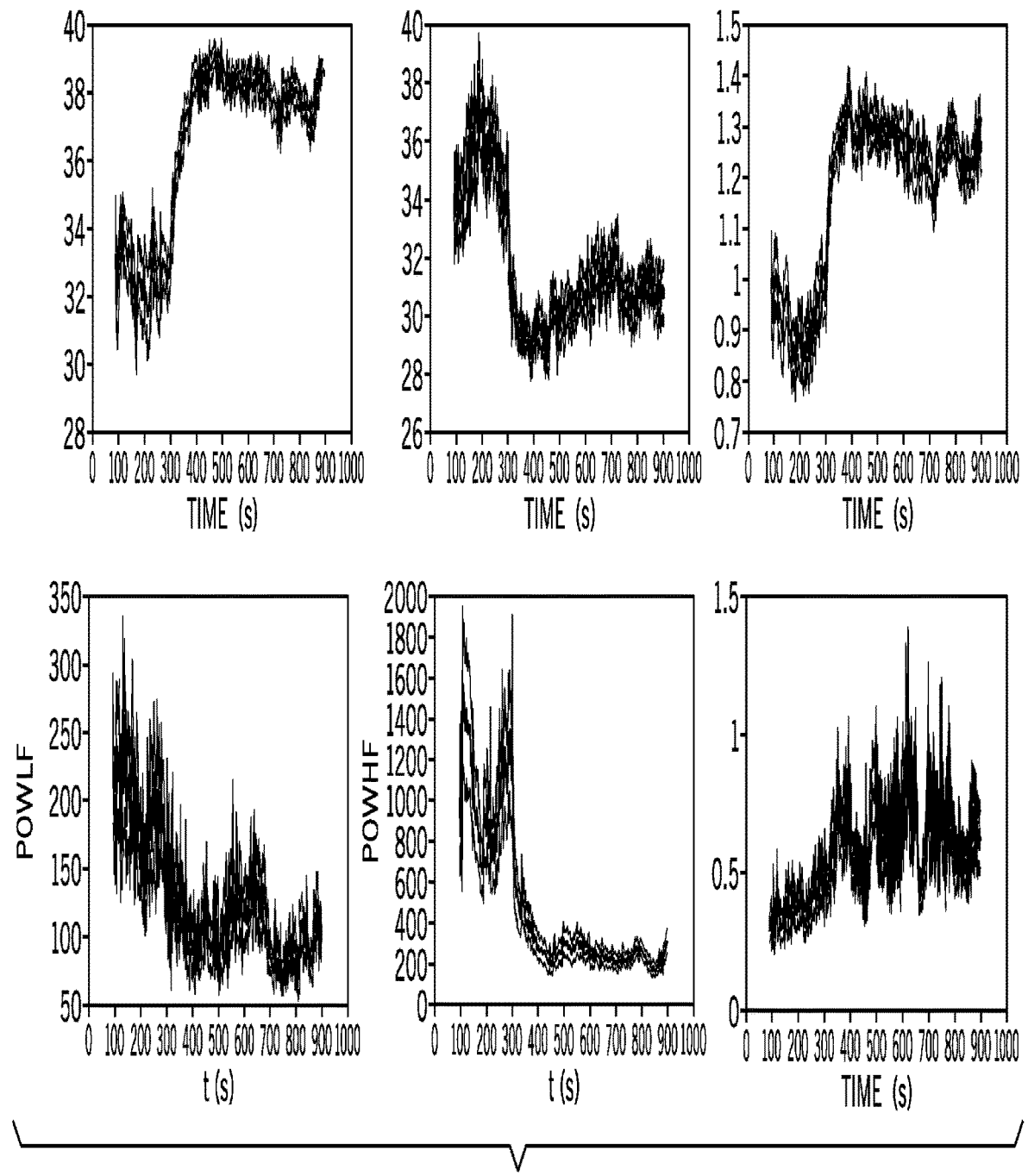
FIG. 6 is a graph representing experimental results of the system of FIG. 1 processing heartbeat data of all subjects of the experiment illustrated in FIG. 5.

The following five tables contain the experimental results of processing the collected data with the system of FIGS. 1 and 2, including a comprehensive assessment of the data by the autonomic assessment module. FIG. 5 illustrates the computed results, for a representative subject of the tilt-table protocol, of the SAI and PAI measured over time, compared with the HF and LF statistical power measurements, the sympatho-vagal balance measurements, and the LF-HF ratio measurements obtained by known analysis methods from the experimental data. FIG. 6 illustrates the computed results (mean and confidence interval) of the same parameters as those of FIG. 5, but for all subjects, which were supine from 0 to 300 secs and upright from 300 to 900 secs in the graph. Expected estimates of sympathetic activity and sympatho-vagal balance during a supine-to-upright (tilting) protocol should show a significant increase during the upright position with respect to the acquisition in supine position. This is due to the increased sympathetic activity occurring during the tilting procedure. FIG. 6 clearly shows how the Sympathetic activity index (SAI) and the sympatho-vagal balance estimates (SAI/PAI) follow such physiological dynamics, while classical power LF and LF/HF ratio do not.

TABLE I

RESULTS FROM THE REST - STAND UP EXPERIMENTAL DATA SET

| Statistical Index | Model | Rest | Stand-Up | P-Value | AUC |
|---|---|---|---|---|---|
| $\mu_{RR}$(ms) | $AR_{PP}$ | 906.17 ± 116.21 | 774.48 ± 80.41 | 0.015907 | 0.743945 |
| | $ARL_{PP}$ | 914.94 ± 122.70 | 773.46 ± 80.67 | 0.011924 | 0.754325 |
| | AR | 910.94 ± 123.08 | 781.92 ± 55.96 | 0.013141 | 0.750865 |
| $\sigma_{RR(NAR)}$ (ms) | $AR_{PP}$ | 19.69 ± 9.37 | 15.84 ± 5.06 | 0.406973 | 0.587891 |
| | $ARL_{PP}$ | 19.72 ± 9.37 | 16.57 ± 4.89 | 0.521672 | 0.568359 |
| | AR | 47.48 ± 18.59 | 48.65 ± 16.42 | 0.998264 | 0.498162 |
| Sympathetic Activity | LF($AR_{PP}$) | 328.54 ± 260.34 | 410.03 ± 305.24 | 0.986259 | 0.503460 |
| | LF($ARL_{PP}$) | 569.52 ± 347.75 | 581.42 ± 422.77 | 0.942562 | 0.509191 |
| | LF(AR) | 349.86 ± 331.22 | 514.13 ± 506.35 | 0.947366 | 0.508170 |
| | NEW(0) | 8.78 ± 1.21 | 12.55 ± 0.87 | 0.000078 | 0.933333 |
| | NEW(1) | 8.52 ± 2.08 | 12.83 ± 0.34 | 0.000155 | 1.000000 |
| | NEW(2) | 9.14 ± 0.87 | 10.11 ± 1.17 | 0.027497 | 0.723183 |
| | NEW(3) | 33.05 ± 5.59 | 43.56 ± 5.15 | 0.000256 | 0.875000 |
| | NEW(4) | 33.70 ± 2.25 | 37.78 ± 1.98 | 0.000256 | 0.875000 |
| Parasympathetic Activity | HF($AR_{PP}$) | 179.39 ± 149.43 | 76.13 ± 51.63 | 0.125312 | 0.655709 |
| | HF($ARL_{PP}$) | 194.05 ± 159.26 | 120.44 ± 65.97 | 0.221391 | 0.624567 |
| | HF(AR) | 234.17 ± 150.02 | 121.52 ± 71.68 | 0.088179 | 0.673010 |
| | NEW(0) | 10.83 ± 1.01 | 7.16 ± 1.97 | 0.001805 | 0.842857 |
| | NEW(1) | 11.37 ± 0.84 | 8.93 ± 1.56 | 0.028127 | 0.828125 |
| | NEW(2) | 11.42 ± 1.09 | 10.00 ± 0.38 | 0.002437 | 0.80622 |
| | NEW(3) | 38.39 ± 3.20 | 32.03 ± 3.74 | 0.002631 | 0.808824 |
| | NEW(4) | 35.23 ± 3.45 | 30.74 ± 3.06 | 0.007283 | 0.775735 |
| Sympatho-Vagal Balance | $AR_{PP}$ | 1.37 ± 0.78 | 2.58 ± 2.41 | 0.221391 | 0.624567 |
| | $ARL_{PP}$ | 1.64 ± 1.09 | 2.77 ± 2.07 | 0.279809 | 0.612132 |
| | AR | 0.87 ± 0.66 | 0.89 ± 0.89 | 0.597419 | 0.553922 |

TABLE I-continued

RESULTS FROM THE REST - STAND UP EXPERIMENTAL DATA SET

| Statistical Index | Model | Rest | Stand-Up | P-Value | AUC |
|---|---|---|---|---|---|
| | NEW(0) | 0.86 ± 0.30 | 1.49 ± 0.17 | 0.002463 | 0.826667 |
| | NEW(1) | 0.81 ± 0.19 | 1.35 ± 0.29 | 0.001088 | 0.953125 |
| | NEW(2) | 0.80 ± 0.14 | 1.12 ± 0.11 | 0.000650 | 0.844291 |
| | NEW(3) | 0.83 ± 0.18 | 1.38 ± 0.23 | 0.000014 | 0.937716 |
| | NEW(4) | 0.95 ± 0.13 | 1.21 ± 0.10 | 0.000020 | 0.937500 |
| RMSSD (ms) | | 26.28 ± 9.78 | 19.46 ± 4.41 | 0.144596 | 0.650735 |
| NN50 (count) | | 17.00 ± 16.00 | 5.00 ± 5.00 | 0.049265 | 0.698962 |
| pNN50 (%) | | 5.98 ± 5.89 | 2.18 ± 2.18 | 0.098656 | 0.665033 |
| HRV_tri_ind | | 8.10 ± 1.71 | 7.61 ± 2.01 | 0.605398 | 0.553633 |
| TINN (ms) | | 147.50 ± 40.00 | 185.00 ± 25.00 | 0.563922 | 0.560662 |

P-values are obtained from the rank-sum test between the Rest and Tilt.
NEW(0): regression with subjective values for the first condition
NEW(1): regression with subjective values for 3 conditions (standup-slow-fast)
NEW(2): regression with general values, i.e. mean of all for 3 conditions (standup-slow-fast)
NEW(3): regression with general values, i.e. mean of all subj from rest-tilt control blockade dataset
NEW(4): regression with general values, i.e. mean of all subj from suppression blockade (parasympathetic suppression → sympathetic regressors % sympathetic suppression → parasympathetic regressors)

TABLE II

RESULTS FROM THE REST - SLOW TILT-TABLE EXPERIMENTAL DATA SET

| Statistical Index | Model | Rest | Titl-Table Slow | P-Value | AUC |
|---|---|---|---|---|---|
| $\mu_{RR}$(ms) | $AR_{PP}$ | 875.25 ± 73.14 | 765.03 ± 58.91 | 0.000512 | 0.831025 |
| | $ARL_{PP}$ | 877.80 ± 72.50 | 764.79 ± 56.81 | 0.000412 | 0.836565 |
| | AR | 879.59 ± 75.09 | 772.82 ± 46.10 | 0.001063 | 0.794312 |
| $\sigma_{RR(NAR)}$ (ms) | $AR_{PP}$ | 21.51 ± 6.07 | 15.13 ± 4.95 | 0.057883 | 0.678947 |
| | $ARL_{PP}$ | 22.29 ± 5.92 | 15.11 ± 4.62 | 0.057883 | 0.678947 |
| | AR | 52.57 ± 17.69 | 62.80 ± 16.30 | 0.843425 | 0.479532 |
| Sympathetic Activity | LF($AR_{PP}$) | 417.76 ± 240.68 | 332.88 ± 162.72 | 0.438254 | 0.422840 |
| | LF($ARL_{PP}$) | 648.32 ± 334.85 | 317.44 ± 83.32 | 0.086005 | 0.333333 |
| | LF(AR) | 465.03 ± 241.99 | 394.37 ± 310.24 | 0.661443 | 0.457064 |
| | NEW(0) | 8.18 ± 1.50 | 11.14 ± 1.48 | 0.000965 | 0.850000 |
| | NEW(1) | 9.22 ± 0.80 | 10.00 ± 1.16 | 0.052808 | 0.754545 |
| | NEW(2) | 9.26 ± 0.56 | 10.52 ± 0.72 | 0.000970 | 0.814404 |
| | NEW(3) | 30.78 ± 5.19 | 35.54 ± 5.45 | 0.011087 | 0.742382 |
| | NEW(4) | 32.79 ± 2.26 | 35.05 ± 2.13 | 0.012048 | 0.739612 |
| Parasympathetic Activity | HF($AR_{PP}$) | 235.59 ± 166.53 | 88.15 ± 68.42 | 0.046554 | 0.692982 |
| | HF($ARL_{PP}$) | 255.41 ± 153.39 | 104.23 ± 43.75 | 0.027886 | 0.716049 |
| | HF(AR) | 263.67 ± 141.88 | 150.51 ± 74.30 | 0.050001 | 0.690058 |
| | NEW(0) | 11.96 ± 2.00 | 7.27 ± 2.58 | 0.000177 | 0.890625 |
| | NEW(1) | 14.09 ± 0.41 | 9.13 ± 2.40 | 0.001355 | 0.918182 |
| | NEW(2) | 11.66 ± 0.93 | 10.25 ± 0.65 | 0.000708 | 0.822715 |
| | NEW(3) | 39.14 ± 2.67 | 36.02 ± 1.01 | 0.066003 | 0.678363 |
| | NEW(4) | 35.03 ± 1.83 | 33.59 ± 1.56 | 0.132882 | 0.648148 |
| Sympatho-Vagal Balance | $AR_{PP}$ | 1.03 ± 0.74 | 2.73 ± 1.64 | 0.209343 | 0.620499 |
| | $ARL_{PP}$ | 1.23 ± 0.66 | 2.25 ± 1.12 | 0.289193 | 0.604938 |
| | AR | 0.66 ± 0.23 | 1.21 ± 0.68 | 0.168735 | 0.635802 |
| | NEW(0) | 0.66 ± 0.19 | 1.51 ± 0.69 | 0.000189 | 0.902222 |
| | NEW(1) | 0.63 ± 0.09 | 1.18 ± 0.33 | 0.000376 | 0.963636 |
| | NEW(2) | 0.82 ± 0.12 | 0.95 ± 0.07 | 0.004746 | 0.765789 |
| | NEW(3) | 0.81 ± 0.20 | 1.05 ± 0.21 | 0.007233 | 0.756233 |
| | NEW(4) | 0.91 ± 0.14 | 1.03 ± 0.08 | 0.008601 | 0.750693 |
| RMSSD (ms) | | 32.10 ± 12.56 | 19.68 ± 4.52 | <0.05 | 0.698830 |
| NN50 (count) | | 31.00 ± 29.00 | 6.00 ± 5.50 | <0.02 | 0.728070 |
| pNN50 (%) | | 10.20 ± 9.47 | 1.74 ± 1.37 | <0.02 | 0.727778 |
| HRV_tri_ind | | 8.03 ± 1.41 | 7.31 ± 1.61 | >0.05 | 0.660819 |
| TINN (ms) | | 195.00 ± 70.00 | 150.00 ± 45.00 | >0.05 | 0.641274 |

P-values are obtained from the rank-sum test between the Rest and Tilt.
NEW(0): regression with subjective values for the first condition
NEW(1): regression with subjective values for 3 conditions (standup-slow-fast)
NEW(2): regression with general values, i.e. mean of all for 3 conditions (standup-slow-fast)
NEW(3): regression with general values, i.e. mean of all subj from rest-tilt control blockade dataset
NEW(4): regression with general values, i.e. mean of all subj from suppression blockade (parasympathetic suppression → sympathetic regressors % sympathetic suppression → parasympathetic regressors)

TABLE III

RESULTS FROM THE REST - FAST TILT-TABLE EXPERIMENTAL DATA SET

| Statistical Index | Model | Rest | Titl-Table Fast | P-Value | AUC |
|---|---|---|---|---|---|
| $\mu_{RR}$(ms) | $AR_{PP}$ | 881.03 ± 94.55 | 776.18 ± 66.49 | 0.004627 | 0.770083 |
| | $ARL_{PP}$ | 883.03 ± 95.78 | 774.62 ± 54.46 | 0.005068 | 0.767313 |
| | AR | 860.50 ± 80.48 | 777.18 ± 51.58 | 0.009375 | 0.751462 |
| $\sigma_{RR(NAR)}$ (ms) | $AR_{PP}$ | 21.68 ± 8.02 | 16.33 ± 4.00 | 0.064190 | 0.682099 |
| | $ARL_{PP}$ | 22.18 ± 8.31 | 16.92 ± 4.51 | 0.073844 | 0.675926 |
| | AR | 48.20 ± 9.40 | 46.00 ± 15.01 | 0.318951 | 0.598765 |
| Sympathetic Activity | LF($AR_{PP}$) | 476.41 ± 285.63 | 349.72 ± 203.75 | 0.303830 | 0.398148 |
| | LF($ARL_{PP}$) | 538.51 ± 279.99 | 384.29 ± 244.51 | 0.149993 | 0.358025 |
| | LF(AR) | 401.86 ± 330.31 | 338.33 ± 278.42 | 0.739734 | 0.533951 |
| | NEW(0) | 10.14 ± 1.30 | 12.21 ± 1.43 | 0.002616 | 0.836735 |
| | NEW(1) | 9.51 ± 0.50 | 12.95 ± 2.07 | 0.013986 | 0.904762 |
| | NEW(2) | 9.33 ± 0.50 | 10.70 ± 0.49 | 0.000156 | 0.870370 |
| | NEW(3) | 33.70 ± 5.42 | 41.42 ± 3.33 | 0.002173 | 0.792244 |
| | NEW(4) | 34.25 ± 2.22 | 37.31 ± 1.19 | 0.001183 | 0.817901 |
| Parasympathetic Activity | HF($AR_{PP}$) | 214.90 ± 159.75 | 123.14 ± 79.59 | 0.103231 | 0.660494 |
| | HF($ARL_{PP}$) | 244.91 ± 169.36 | 130.95 ± 65.16 | 0.178741 | 0.632716 |
| | HF(AR) | 296.05 ± 153.27 | 136.80 ± 59.81 | 0.023688 | 0.722222 |
| | NEW(0) | 10.77 ± 0.81 | 8.17 ± 1.90 | 0.001019 | 0.867347 |
| | NEW(1) | 11.59 ± 0.91 | 8.56 ± 1.48 | 0.002331 | 0.959184 |
| | NEW(2) | 11.69 ± 1.39 | 10.46 ± 0.67 | 0.027591 | 0.713450 |
| | NEW(3) | 39.13 ± 3.15 | 34.12 ± 1.84 | 0.002259 | 0.795322 |
| | NEW(4) | 36.12 ± 1.63 | 30.89 ± 1.05 | 0.000075 | 0.899654 |
| Sympatho-Vagal Balance | $AR_{PP}$ | 2.05 ± 1.57 | 1.96 ± 1.26 | 0.753865 | 0.532680 |
| | $ARL_{PP}$ | 1.76 ± 0.91 | 1.71 ± 1.18 | 0.936956 | 0.490741 |
| | AR | 0.93 ± 0.46 | 1.51 ± 1.10 | 0.116943 | 0.656863 |
| | NEW(0) | 0.83 ± 0.35 | 1.74 ± 0.47 | 0.000612 | 0.876190 |
| | NEW(1) | 0.85 ± 0.18 | 1.57 ± 0.31 | 0.011072 | 0.897959 |
| | NEW(2) | 0.84 ± 0.16 | 1.03 ± 0.07 | 0.000977 | 0.818713 |
| | NEW(3) | 0.94 ± 0.22 | 1.25 ± 0.13 | 0.000704 | 0.827485 |
| | NEW(4) | 0.95 ± 0.13 | 1.23 ± 0.06 | 0.000329 | 0.842105 |
| RMSSD (ms) | | 28.70 ± 11.32 | 18.10 ± 3.60 | 0.038235 | 0.703704 |
| NN50 (count) | | 28.00 ± 26.00 | 3.00 ± 3.00 | 0.002547 | 0.795666 |
| pNN50 (%) | | 6.54 ± 6.18 | 1.14 ± 1.14 | 0.018120 | 0.735294 |
| HRV_tri_ind | | 8.49 ± 2.00 | 6.50 ± 0.93 | 0.062213 | 0.686275 |
| TINN (ms) | | 182.50 ± 60.00 | 140.00 ± 45.00 | 0.160440 | 0.640523 |

P-values are obtained from the rank-sum test between the Rest and Tilt.
NEW(0): regression with subjective values for the first condition
NEW(1): regression with subjective values for 3 conditions (standup-slow-fast)
NEW(2): regression with general values, i.e. mean of all for 3 conditions (standup-slow-fast)
NEW(3): regression with general values, i.e. mean of all subj from rest-tilt control blockade dataset
NEW(4): regression with general values, i.e. mean of all subj from suppression blockade (parasympathetic suppression → sympathetic regressors % sympathetic suppression → parasympathetic regressors)

Additionally, the six application-specific modules described above have been extensively tested to be applied on (a) tilt studies in healthy subjects and subjects with autonomic dysfunctions, demonstrating improvement of the separate Sympatho-vagal assessment by the SAI/PAI signals as compared with existing state-of-the-art methods; (b) data recorded during anesthesia studies in ICU settings, demonstrating the system's efficacy in clinical settings and providing important evidence of the potential usefulness of including the application in recording and control devices aimed at monitoring the patient's stay in the hospital and anesthesia procedures in the operating room; (c) sleep studies, demonstrating improved classification power in sleep scoring; (d) relaxation and stress elicitation protocols, demonstrating improved instantaneous classification of basic states of arousal; (d) emotional elicitation protocols, demonstrating improved instantaneous classification of basic emotional states; and (e) data during exercise and recovery from exercise in healthy controls and subjects in different cardiovascular conditions.

Table VI reports the results of an exemplary sleep study using the system of FIGS. 1 and 2 and the sleep monitor module to process heartbeat data collected during sleep. Thirteen subjects were tested, with 30 second segments of heartbeat data being recorded throughout the eight hours (average time) that the subjects slept. The sleep monitor module configured the autonomic assessment module to classify the recorded segments as occurring during a rapid-eye-movement (REM) state or non-REM state. In this exemplary pilot application, the classification accuracy of the system outperforms known systems.

TABLE VI

SLEEP MONITORING ASSESSMENT RESULTS

| Subject | # Segments | # Correct | Accuracy (%) |
|---|---|---|---|
| Subject 1 | 730 | 616 | 84.4 |
| Subject 2 | 886 | 675 | 76.2 |
| Subject 3 | 960 | 791 | 82.4 |
| Subject 4 | 958 | 763 | 79.6 |
| Subject 5 | 618 | 487 | 78.8 |
| Subject 6 | 901 | 770 | 85.5 |
| Subject 7 | 960 | 814 | 84.8 |
| Subject 8 | 886 | 665 | 75.0 |
| Subject 9 | 568 | 477 | 84.0 |
| Subject 10 | 796 | 633 | 79.5 |
| Subject 11 | 723 | 600 | 83.0 |
| Subject 12 | 709 | 562 | 79.3 |
| Subject 13 | 917 | 755 | 82.3 |

Figure 7:
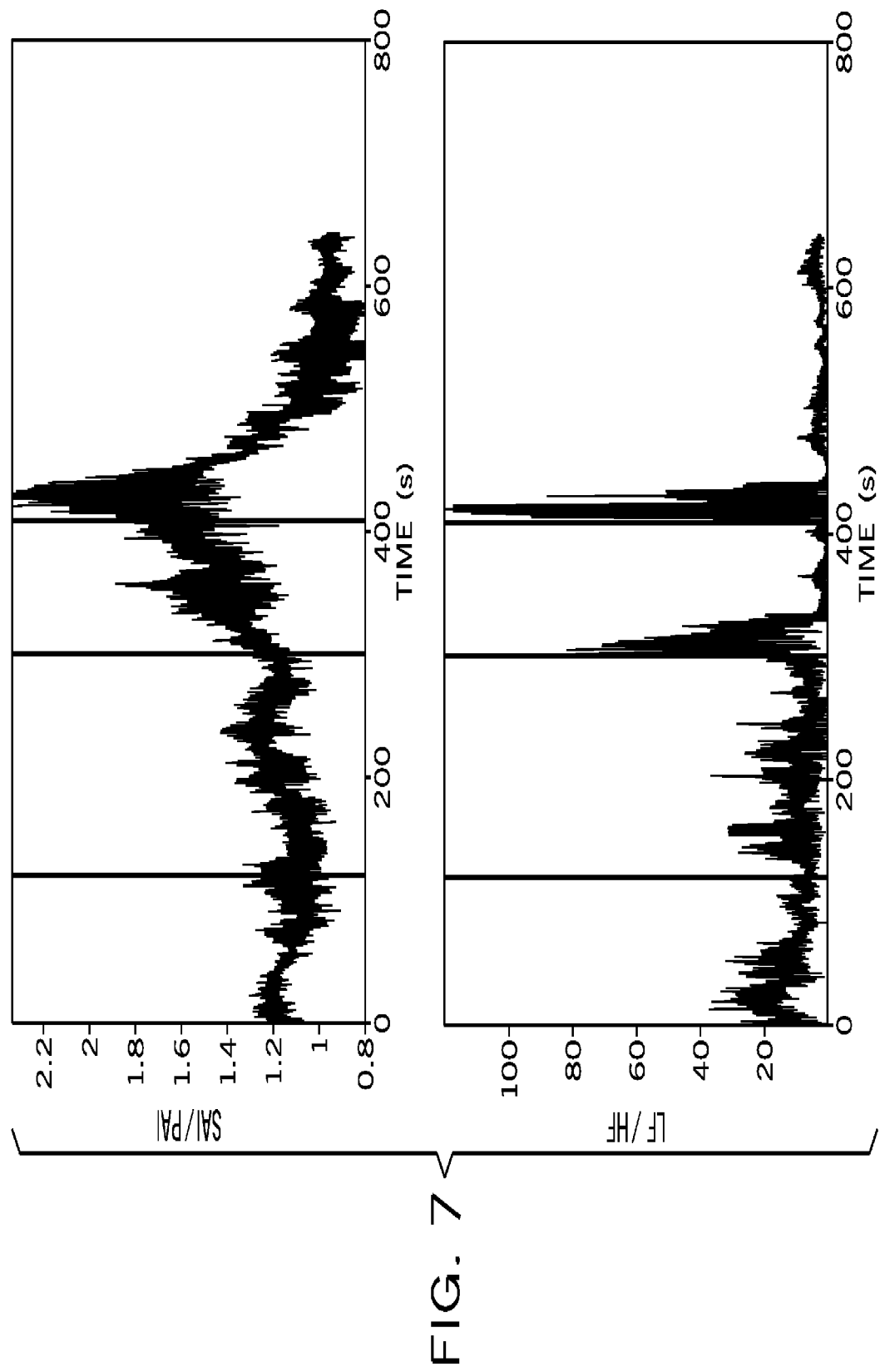
FIG. 7 is a graph representing exemplary experimental results of the system of FIG. 1 processing heartbeat data of subjects undergoing a physical activity assessment.

FIG. 7 illustrates comparative results of an exemplary physical activity assessment using the system of FIGS. 1 and 2 and the physical activity monitor module to process heartbeat data collected from 10 subjects during a period (about 650 secs) of strenuous exercise. The black line indicates the median value of the classic LF/HF index and the SAI/PAI ratio. Confidence intervals are shown in gray. Vertical lines indicate the end of three consecutive exercise sessions at increasing loads. Note the significant improvement in the estimation accuracy of the sympathetic activity along the time period, accompanied by a consistent decrease of inter-subject variability.

What is claimed is:

1. A computing device, comprising:
   an input device interface configured to receive an input signal comprising subject heartbeat data recorded from a subject;
   a processor in signal communication with the input device interface; and
   memory storing program instructions;
   the processor executing the program instructions to:
      determine a set of heartbeat events from the subject heartbeat data, the heartbeat events including a plurality of past R-R intervals;
      generate a first model of a mean heart rate of the subject, the first model comprising a modeling function that includes:
         a time-varying zero-order autoregressive coefficient;
         a sympathetic component representing an influence on the mean heart rate of the subject's sympathetic nerve activity, the sympathetic component comprising a first sum, computed at a first frequency, of a time-varying first-order autoregressive coefficient multiplying a Laguerre expansion of the plurality of past R-R intervals; and
         a parasympathetic component representing an influence on the mean heart rate of the subject's parasympathetic nerve activity, the parasympathetic component comprising a second sum, computed at a second frequency, of the first-order autoregressive coefficient multiplying the Laguerre expansion;
      the first model further having a modeling structure including a first function of the first-order autoregressive coefficient within the sympathetic component, and a second function of the first-order autoregressive coefficient within the parasympathetic component;
      calculate a plurality of recursive parameter estimations of the first function to generate a first time-varying estimation of the modeling structure;
      calculate a plurality of recursive parameter estimations of the second function to generate a second time-varying estimation of the modeling structure;
      determine a first multiple regression of the first function to generate a first disentangling coefficient;
      determine a second multiple regression of the second function to generate a second disentangling coefficient;
      determine a sympathetic activity index value in a sympathetic activity index (SAI) defined by a SAI function that includes the first disentangling coefficient and the first time-varying estimation of the modeling structure; and
      determine a parasympathetic activity index value in a parasympathetic activity index (PAI) defined by a PAI function that includes the second disentangling coefficient and the second time-varying estimation of the modeling structure.

2. The computing device of claim 1, wherein the computing device further executes the program instructions to compare the set of heartbeat events to a second model generated from a reference heartbeat dataset to generate the zero-order autoregressive coefficient and the first-order autoregressive coefficient.

3. The computing device of claim 2, wherein the reference heartbeat dataset comprises total autonomic modulation data, sympathetic activity only data, and parasympathetic activity only data, and wherein the computing device further executes the program instructions to generate the second model.

4. The computing device of claim 1, wherein the computing device further executes the program instructions to determine an instantaneous estimate of an R-R mean value without interpolation of the R-R mean value between a first arrival time of a first heart beat and a second arrival time of a second heart beat that arrives sequentially after the first heart beat, the R-R mean value having a time scale measurable in milliseconds.

5. The computing device of claim 1, wherein the computing device further executes the program instructions to:
   determine that the SAI value or the PAI value corresponds to a condition of the subject; and
   perform an action that is indicated to be performed by the computing device when the condition is present in the subject.

6. A method, comprising:
   obtaining a set of heartbeat events including a plurality of past R-R intervals;
   generating a first model of a mean heart rate from the set of heartbeat events, the first model comprising:
      a sympathetic component representing an influence of sympathetic nerve activity on the mean heart rate, the sympathetic component comprising a time-varying first autoregressive coefficient and a Laguerre expansion of the plurality of past R-R intervals;
      a parasympathetic component representing an influence of parasympathetic nerve activity on the mean heart rate, the parasympathetic component comprising a time-varying second autoregressive coefficient and the Laguerre expansion; and
      a modeling structure including a first function of the first autoregressive coefficient and a second function of the second autoregressive coefficient;
   determining a sympathetic activity index value in a sympathetic activity index (SAI) that is based on the first function; and
   determining a parasympathetic activity index value in a parasympathetic activity index (PAI) that is based on the second function.

7. The method of claim 6, further comprising:
   calculating a plurality of recursive parameter estimations of the first function to generate a first time-varying estimation of the modeling structure, the SAI being based on the first time-varying estimation; and
   calculating a plurality of recursive parameter estimations of the second function to generate a second time-varying estimation of the modeling structure, the PAI being based on the second time-varying estimation.

8. The method of claim 6, further comprising determining at least one multiple regression of the modeling structure to generate a first disentangling coefficient and a second disentangling coefficient, the SAI being further based on the first disentangling coefficient, and the PAI being further based on the second disentangling coefficient.

9. A system for monitoring a condition of a patient comprising:
   an input configured to receive a signal indicative of a heartbeat of a subject;

a processor in communication with the input to receive the signal and configured to:
  analyze the signal to identify an autonomic state of the subject by evaluating sympathetic and parasympathetic activity of the subject;
  using a predetermined model and the autonomic state, generate an index of dynamics of two autonomic branches; and
  generate a report of a current condition of the subject based on the index.

10. The system of claim 9, wherein the predetermined model includes a decisional tree structure.

11. The system of claim 9, wherein the input signal is applied to a series of program modules to generate the report.

12. The system of claim 11, further comprising a program memory accessible by the processor and a first module configured to cause the processor to determine a desired matching base function for the input heartbeat using reference heartbeats stored in the program memory.

13. The system of claim 12, further comprising a second module to cause the processor to perform a time-varying estimation that calculates a sympathetic autonomic index (SAI) and parasympathetic autonomic index (PAI) for a selected time period.

14. The system of claim 13, further comprising a third module to cause the processor to utilize the SAI and PAI to detect a predetermined activity.

15. The system of claim 13, wherein the SAI and PAI provide markers associated with the independent dynamics of the two autonomic branches.

16. The system of claim 9, wherein the predetermined model includes a sympathetic component representing an influence of sympathetic nerve activity on the signal indicative of the heartbeat of the subject and a parasympathetic component representing an influence of parasympathetic nerve activity on the signal indicative of the heartbeat of the subject.

17. The system of claim 9, wherein the report indicates at least sympathetic and parasympathetic activity of the subject.

* * * * *